(12) United States Patent
Cohen et al.

(10) Patent No.: US 10,082,503 B2
(45) Date of Patent: Sep. 25, 2018

(54) IDENTIFYING ANTIGEN CLUSTERS FOR MONITORING A GLOBAL STATE OF AN IMMUNE SYSTEM

(71) Applicant: YEDA RESEARCH AND DEVELOPMENT CO. LTD., Rehovot (IL)

(72) Inventors: Irun R. Cohen, Rehovot (IL); Eytan Domany, Rehovot (IL); Francisco Javier Quintana, Jamaica Plain, MA (US); Guy Hed, Rehovot (IL); Gad Getz, Haifa (IL)

(73) Assignee: YEDA RESEARCH AND DEVELOPMENT CO. LTD. (IL)

( * ) Notice: Subject to any disclaimer, the term of this patent is extended or adjusted under 35 U.S.C. 154(b) by 1183 days.

(21) Appl. No.: 14/210,409

(22) Filed: Mar. 13, 2014

(65) Prior Publication Data
US 2014/0200159 A1   Jul. 17, 2014

Related U.S. Application Data

(60) Division of application No. 13/207,486, filed on Aug. 11, 2011, now Pat. No. 8,703,654, which is a division of application No. 12/357,449, filed on Jan. 22, 2009, now Pat. No. 8,010,298, which is a continuation of application No. 10/332,241, filed as application No. PCT/IL01/00660 on Jul. 18, 2001, now abandoned.

(51) Int. Cl.
| | |
|---|---|
| *G06F 19/24* | (2011.01) |
| *G01N 33/564* | (2006.01) |
| *G01N 33/68* | (2006.01) |
| *G06F 19/18* | (2011.01) |

(52) U.S. Cl.
CPC ....... *G01N 33/564* (2013.01); *G01N 33/6803* (2013.01); *G06F 19/18* (2013.01); *G06F 19/24* (2013.01)

(58) Field of Classification Search
None
See application file for complete search history.

(56) References Cited

U.S. PATENT DOCUMENTS

| | | |
|---|---|---|
| 3,849,550 A | 11/1974 | Teitelbaum |
| 5,114,844 A | 5/1992 | Cohen |
| 5,326,357 A | 7/1994 | Kandel |
| 5,578,303 A | 11/1996 | Cohen |
| 5,671,848 A | 9/1997 | Cohen |
| 5,763,158 A | 6/1998 | Bohannon |
| 5,780,034 A | 7/1998 | Cohen |
| 5,800,808 A | 9/1998 | Konfino |
| 5,858,804 A | 1/1999 | Zanzucchi |
| 5,981,700 A | 11/1999 | Rabin |
| 6,048,898 A | 4/2000 | Konfino |
| 6,054,430 A | 4/2000 | Konfino |
| 7,276,341 B2 | 10/2007 | Harley |
| 8,010,298 B2 | 8/2011 | Cohen |
| 2003/0003516 A1* | 1/2003 | Robinson ........... A61K 39/0008 435/7.9 |
| 2004/0014069 A1 | 1/2004 | Cohen |
| 2005/0260770 A1 | 11/2005 | Cohen |
| 2009/0258790 A1 | 10/2009 | Cohen |

FOREIGN PATENT DOCUMENTS

| | | |
|---|---|---|
| EP | 0417271 | 12/1998 |
| WO | 99/39210 | 8/1999 |
| WO | 02/08755 | 1/2002 |

OTHER PUBLICATIONS

Grus et al (1998 Ocular Immunology and Inflammation 6:43-50).*
Kupinski et al (1999 IEEE Transactions on Medical Imaging 18:675-85).*
Abulafia-Lapid et al., (1999) T cell proliferative responses of type 1 diabetes patients and healthy individuals to human hsp60 and its peptides. J Autoimmun 12(2): 121-9.
Abulafia-Lapid et al., (2003) T cells and autoantibodies to human HSP70 in type 1 diabetes in children. J Autoimmun 20(4): 313-21.
Alon et al., (1999) Broad patterns of gene expression revealed by clustering analysis of tumor and normal colon tissues probed by oligonucleotide arrays. Proc Natl Acad Sci U S A 96(12): 6745-50, p. 6749 r-h Col.
Batstra et al., (2001) Prediction and diagnosis of type 1 diabetes using beta-cell autoantibodies. Clin Lab 47(9-10): 497-507, abstract.
Cahill (2000) Protein arrays: a high-throughput solution for proteomics research? Trends in Biotechnology 18: 47-51.
Domany (1999) Superparamagnetic clustering of data—The definitive solution of an ill-posed problem. Physica A: Statistical Mechanics and its Applications 263(1-4): 158-169, pp. 166-168.
Eisen et al., (1998) Cluster analysis and display of genome-wide expression patterns. Proc Natl Acad Sci U S A 95 (25): 14863-8.
Ferreira et al., (1997) Instability of natural antibody repertoires in systemic lupus erythematosus patients, revealed by multiparametric analysis of serum antibody reactivities. Scand J Immunol 45(3): 331-41.
Fraley and Raftery (1998) How many clusters? Which clustering method? Answers via model-based cluster analysis. Technical report No. 329, Department of Statistics, University of Washington, Seattle, WA, P.I, 1-19.
Getz et al., (2000) Coupled two-way clustering analysis of gene microarray data. Proc Natl Acad Sci U S A 97(22): 12079-84.
Golub et al., (1999) Molecular classification of cancer: class discovery and class prediction by gene expression monitoring. Science 286(5439): 531-7.
Ito et al., (1992) Cell proliferation in childhood acute leukemia. Comparison of Ki-67 and proliferating cell nuclear antigen immunocytochemical and DNA flow cytometric analysis. Cancer 69(8): 2176-82.

(Continued)

*Primary Examiner* — Christopher M Gross
(74) *Attorney, Agent, or Firm* — J.A. Lindeman & Co., PLLC

(57) ABSTRACT

Method, system and an article of manufacture for clustering and thereby identifying predefined antigens reactive with undetermined immunoglobulins of sera derived from patient subjects in need of diagnosis of disease or monitoring of treatment.

20 Claims, 11 Drawing Sheets

(56) References Cited

OTHER PUBLICATIONS

Joos et al., (2000) A microarray enzyme-linked immunosorbent assay for autoimmune diagnostics. Electrophoresis 21(13): 2641-50.

Könen-Waisman et al., (1995) Self and foreign 60-kilodalton heat shock protein T cell epitope peptides serve as immunogenic carriers for a T cell-independent sugar antigen. J Immunol 154(11): 5977-85.

Lieberman and DiLorenzo (2003) A comprehensive guide to antibody and T-cell responses in type 1 diabetes. Tissue Antigens 62(5): 359-77.

Lossos et al., (1998) Anticardiolipin antibodies in acute myeloid leukemia: prevalence and clinical significance. Am J Hematol 57(2): 139-43.

Mor et al., (1996) IL-2 and TNF receptors as targets of regulatory T-T interactions: isolation and characterization of cytokine receptor-reactive T cell lines in the Lewis rat. J Immunol 157(11): 4855-61.

Oliva et al., (1998) Automated classification of antibody complementarity determining region 3 of the heavy chain (H3) loops into canonical forms and its application to protein structure prediction. J Mol Biol 279(5): 1193-210, pp. 1193-1194.

Pal et al., (2000) Identification and purification of cytolytic antibodies directed against O-acetylated sialic acid in childhood acute lymphoblastic leukemia. Glycobiology 10(6): 539-49.

Quintana et al., (2003) Cluster analysis of human autoantibody reactivities in health and in type 1 diabetes mellitus: a bioinformatic approach to immune complexity. J Autoimmun 21(1): 65-75.

Quintana et al., (2004) Functional immunomics: microarray analysis of IgG autoantibody repertoires predicts the future response of mice to induced diabetes. Proc Natl Acad Sci U S A 101(suppl 2): 14615-21.

Robinson et al., (2002) Autoantigen microarrays for multiplex characterization of autoantibody responses. Nat Med 8(3): 295-301.

Robinson et al., (2003) Protein microarrays guide tolerizing DNA vaccine treatment of autoimmune encephalomyelitis. Nat Biotechnol 21(9): 1033-9.

\* cited by examiner

IDENTIFYING ANTIGEN CLUSTERS FOR MONITORING A GLOBAL STATE OF AN IMMUNE SYSTEM

RELATED APPLICATIONS

This Application is a Divisional of U.S. patent application Ser. No. 13/207,486 (published as US 2011/0301065) filed Aug. 11, 2011, which is a Divisional of U.S. patent application Ser. No. 12/357,449 (issued as U.S. Pat. No. 8,010, 298) filed Jan. 22, 2009, which is a Continuation of U.S. patent application Ser. No. 10/332,241 filed Jan. 6, 2003, now abandoned, which is a National Phase of PCT Patent Application No. PCT/IL01/00660 having International filing date of Jul. 18, 2001, which claims the benefit of Israel Patent Application No. 137460 filed on Jul. 24, 2000, the contents of each of which are incorporated herein by reference in their entireties.

FIELD AND BACKGROUND OF THE INVENTION

The present invention relates to a method, system and an article of manufacture for clustering and thereby identifying predefined binding moieties of one type which are reactive with undetermined binding moieties of a second type. More particularly, the present invention relates to a method, system and an article of manufacture for clustering and thereby identifying predefined antigens reactive with undetermined immunoglobulins of sera derived from patient subjects in need of diagnosis of disease or monitoring of treatment.

Autoimmune diseases are caused by an attack of a patient's own immune system against otherwise healthy self components of the body. Autoimmune diseases include, for example, type 1 diabetes, Bechet's disease, multiple sclerosis, rheumatoid arthritis, idiopathic thrombocytopenic purpura and various diseases affecting every organ and almost every cell type in the body. These diseases tend to run a relapsing or chronic course, and in many cases affect young individuals in the prime of life. The various autoimmune diseases are often difficult to diagnose early in their course because the clinical picture can, at times, be obscure at onset. It is even more difficult to identify incipient disease in persons at risk. Diagnosis and early diagnosis prior to accumulation of irreversible damage, is becoming more critical because specific immune therapies are now being implemented. To this end, see for example, U.S. Pat. Nos. 5,114,844; 5,671,848; 5,578,303; 5,780,034 and EP 0417271 with respect to IDDM, and Cop-1 in MS (U.S. Pat. Nos. 3,849,550; 5,800,808; 6,048,898; and 6,054,430, which is incorporated herein by reference. The earlier immune treatments are instituted, the more effective they can be.

Traditionally, immunologic diagnosis has been based on an attempt to correlate each disease with a specific immune reactivity, such as an antibody or a T-cell response to a single antigen specific for the disease entity. This approach has been largely unsuccessful for three main reasons: First, a specific antigen or antigens have not been identified for the disease, as is the case in, for example, Bechet's disease, rheumatoid arthritis (1). Second, immunity to multiple self-antigens, and not to a single self-antigen, is manifest in various patients suffering from a single disease. For example, a dozen different antigens are associated with type 1 diabetes (2). Third, a significant number of healthy individuals may manifest antibodies or T-cell reactivities to self-antigens targeted in autoimmune diseases, such as insulin, DNA, myelin basic protein, thyroglobulin and others. Hence, there is a real danger of making a false diagnosis based on the determination of a single immune reactivity. Novel approaches, therefore, are needed to support the diagnoses of specific autoimmune diseases in a way that would justify specific therapeutic interventions.

Chronic diseases that are not thought to be autoimmune are also in need of new diagnostic methods. Many chronic conditions, such as Alzheimer's disease of the brain, various dystrophies of the muscles, psoriasis of the skin, and others, involve inflammation, and one needs convenient tools to help categorize different types of inflammation. These conditions include degenerative and metabolic diseases. Inflammation is also a key factor in transplantation reactions, in healing and in tissue regeneration. The challenge is not only to diagnose the disease, but also to distinguish individuals who would benefit from a particular treatment from those individuals who would not.

Infectious diseases, too, require better diagnostic discrimination between persons who will be susceptible to a particular treatment and persons who will not respond thereto. Certain infections can trigger autoimmune responses, and it is important to be able to diagnose persons who are destined to develop autoimmune diseases.

The immunotherapy of cancer is another situation in which it would be advantageous to classify persons with different types of immune reactivities to self-antigens; many, if not most tumor-associated antigens are self-antigens. Thus, it could be important in the design of therapeutic tumor vaccines to know what kind of autoimmune reactivity is found in the patient.

The immune system regulates inflammation and the state of the immune system to reflects the state of the body in many different conditions. Thus, it is evident that assays for monitoring the state of the immune system are needed. Various immunologic therapies are now being used. There is a critical need to develop markers that will enable the physician to monitor the response of the immune system to various treatments designed to arrest chronic inflammation and autoimmune diseases, vaccinate against infectious agents, or effect the immunotherapy of cancer.

Immune diagnosis and immune monitoring require ways to ascertain the state of an individual's immune system, and to record the dynamic evolution of changes induced by the various therapeutic interventions. Tools for diagnosis and monitoring are likely to require the integration of large amounts of information for the following reasons:

First, the human immune system is enormously complex and its long-term behavior is not easily explained by any particular genes or clones of cells in isolation. For example, it is now known that many autoimmune diseases involve collectives of self-antigens and collective cross-regulation. Indeed, effective tumor immunotherapy may require controlled autoimmunity, and assays for the global state of autoimmunity are therefore essential.

Second, immune system behavior depends on the state of multiple regulatory mechanisms, and not merely on the recognition of one or another antigen.

Third, individual persons, because of their genetic make-up and their varying immune histories are likely to require individualized therapies. The type, amount and schedule of immune regulation or vaccination must be tailored to the needs of the individual.

Thus, the complexity of the immune system is such that one must develop bio-informatic methods that will allow a physician to monitor conveniently the global state of the patient's immune system in health, disease and therapeutic intervention. Such a novel approach is described herein.

In the past, attempts have been made to detect the changes that the immune system undergoes in pathological conditions, with the hope that understanding such changes would lead to a better diagnosis and treatment of patients suffering from autoimmune disorders. In the simplest approach, these efforts have concentrated on the detection of specific antibodies directed to single antigens thought to be relevant to the particular disease (3). Many factors have rendered these attempts unsuccessful. Among them are the low prevalence of the studied antibody reactivities in the patient population, associated with large individual variations that can be observed among patients suffering from the same disease (4). Furthermore, natural auto-antibodies directed against the test antigens are often detected in the sera of healthy individuals (5), complicating the use of these discrete antigen-antibody methods for diagnostic purposes.

Other studies have focused on poly-reactive antibodies each able to recognize a number of different self-antigens. These poly-reactive antibodies, however, have been found both in healthy persons and in patients undergoing autoimmune or tumor-associated processes (6, 7). Therefore, several attempts were made to analyze fluctuations in the levels of auto-reactive antibodies, and changes in the repertoire of recognized antigens. These assays were mainly based on western-blotting techniques directed to simultaneously follow antibody reactivities to several auto-antigens.

The Immunoblotting and Densitometric Subtraction Method was developed as a technique for immunoblotting analysis of the reactions of natural autoantibodies in whole sera of patients (8). By densitometric subtraction, natural autoantibodies present in healthy individuals were differentiated from disease-associated autoantibodies. This method is, however, limited to a few antigens and it does not solve the problem of variation among different experiments which is inherent to blot techniques.

Another method developed to detect antibody repertoires is the Multiple Spot Immunoassay, which assays the reactivities towards 42 different antigens coated onto nitrocellulose, in a western blot procedure (9). The antibody staining in this system is analyzed, and the amount of antibody to the antigens can be semi-quantified, using IgG standards. This method allows rapid screening of auto-antibodies but does not solve the problem of auto-antibodies found in healthy persons. Moreover, it does not solve the intrinsic variation associated with the western blot technique.

Currently, the principle technique in use for assaying antibody patterns is the Panama Blot System. This too is a western-blot system, and it is based on the blotting of undefined tissue extracts. The Panama Blot employs double staining of nitrocellulose membranes to reveal both antibody reactivities and the migration to position of the blotted proteins in the membrane (10, 11). This double staining allows the standardization of the results obtained for each patient. However, since the antigens used in the method are complex mixtures extracted from different tissues, they are not at all identified. Thus, this approach, even while facing the central problem of test variation, does not provide accurate information about the specific antigens recognized; it merely reveals patterns of reactivities, whose targets are totally unknown. The blots tend to vary from test to test, according to the ill-defined tissue extraction and the varying separation of the proteins. Indeed, several different antigens are undoubtedly present in each band.

As an alternative approach, some groups have studied natural auto-antibody reactivity towards panels of selected auto-antigens by means of enzyme immunoassay analysis. However, in order to get meaningful results in these studies, it was necessary to purify various antibody isotypes (12, 13). This purification step by itself, however, invalidates any possible physiological interpretation of the results because the analyzed sample does not reflect the in vivo situation, where different antibody isotypes are mixed and regulate each other (14). Therefore results obtained by this technique are deeply modified by the observer, ruling out any possible application in the management of patient treatment.

There is thus a widely recognized need for, and it would be highly advantageous to have, objective means with which one can diagnose autoimmune diseases and other diseases characterized by an inherent or induced impaired immune system, devoid of the above limitations.

SUMMARY OF THE INVENTION

According to one aspect of the present invention there is provided a method of classifying into a predefined first situation of at least two distinct situations, a binding pattern of a plurality of undetermined first binding moieties, the plurality of undetermined first binding moieties being derived from a first group of objects being associated with the predefined first situation and from at least one second group of objects being associated with a situation other than the first situation of the at least two distinct situations, to a predefined set of a plurality of potential second binding moieties, the method comprising the steps of (a) assaying the plurality of to undetermined first binding moieties of the first group of objects for binding to each of the plurality of potential second binding moieties; (b) assaying the plurality of undetermined first binding moieties of the at least one second group of objects for binding to each of the plurality of potential second binding moieties; and (c) clustering at least some of the plurality of potential second binding moieties into clusters of second binding moieties which bind first binding moieties of the undetermined first binding moieties from the first group of objects, thereby classifying into the predefined first situation the binding pattern of the plurality of undetermined first binding moieties of the objects being associated with the predefined first situation to the predefined set of the plurality of potential second binding moieties.

According to this aspect of the present invention there is also provided a system for classifying into a predefined first situation of at least two distinct situations, a binding pattern of a plurality of undetermined first binding moieties, the plurality of undetermined first binding moieties being derived from a first group of objects being associated with the predefined first situation and from at least one second group of objects being associated with a situation other than the first situation of the at least two distinct situations, to a predefined set of a plurality of potential second binding moieties, the system comprising a data acquisition device and a computation device communicating therewith, the data acquisition device and the computation device being designed, constructed and configured for (a) assaying the plurality of undetermined first binding moieties of the first group of objects for binding to each of the plurality of potential second binding moieties; (b) assaying the plurality of undetermined first binding moieties of the at least one second group of objects for binding to each of the plurality of potential second binding moieties; and (c) clustering at least some of the plurality of potential second binding moieties into clusters of second binding moieties which bind first binding moieties of the undetermined first binding moieties from the first group of objects, thereby classifying into the predefined first situation the binding pattern of the plurality of undetermined first binding moieties of the objects being associated with the predefined first situation to the predefined set of the plurality of potential second binding moieties.

According to another aspect of the present invention there is provided a method of classifying a specific object into a situation of at least two distinct situations, the method comprising the steps of (a) classifying binding patterns of a plurality of undetermined first binding moieties, the plurality of undetermined first binding moieties being derived from a first group of objects being associated with a predefined first situation of the at least two distinct situations, and from at least one second group of objects being associated with a situation other than the first situation of the at least two distinct situations, to a predefined set of a plurality of potential second binding moieties by clustering at least some of the plurality of potential second binding moieties into a cluster of second binding moieties which bind first binding moieties of the undetermined first binding moieties from the first group of objects; and (b) using the cluster for determining whether the specific object is classifiable into the situation of the at least two distinct situations.

According to this aspect of the present invention there is also provided a system for classifying a specific object into a situation of at least two distinct situations, the system comprising a data acquisition device and a computation device communicating therewith, the data acquisition device and the computation device being designed, constructed and configured for (a) classifying binding patterns of a plurality of undetermined first binding moieties, the plurality of undetermined first binding moieties being derived from a first group of objects being associated with a predefined first situation of the at least two distinct situations, and from at least one second group of objects being associated with a situation other than the first situation of the at least two distinct situations, to a predefined set of a plurality of potential second binding moieties by clustering at least some of the plurality of potential second binding moieties into a cluster of second binding moieties which bind first binding moieties of the undetermined first binding moieties from the first group of objects; and (b) using the cluster for determining whether the specific object is classifiable into the situation of the at least two distinct situations.

According to further features in preferred embodiments of the invention described below, the step of clustering at least some of the plurality of potential second binding moieties into clusters of second binding moieties which bind first binding moieties of the undetermined first binding moieties from the first group of objects is effected by a supervised classifier.

According to still further features in the described preferred embodiments the supervised classifier is a neural network algorithm.

According to still further features in the described preferred embodiments the step of clustering at least some of the plurality of potential second binding moieties into clusters of second binding moieties which bind first binding moieties of the undetermined first binding moieties from the first group of objects is effected by a unsupervised classifier.

According to still further features in the described preferred embodiments the unsupervised classifier is a coupled two way clustering algorithm.

According to still further features in the described preferred embodiments, the method further comprising the step of scanning the second binding moieties which bind first binding moieties of the undetermined first binding moieties from the first group of objects and selecting for a subset of the second binding moieties resulting in an optimal sensitivity.

According to still further features in the described preferred embodiments, the method further comprising the step of scanning the second binding moieties which bind first binding moieties of the undetermined first binding moieties from the first group of objects and selecting for a subset of the second binding moieties resulting in an optimal specificity.

According to still further features in the described preferred embodiments, the method further comprising the step of scanning the second binding moieties which bind first binding moieties of the undetermined first binding moieties from the first group of objects and selecting for a subset of the second binding moieties resulting in an optimal specificity and an optimal sensitivity.

According to still further features in the described preferred embodiments, the first binding moieties are immunoglobulins, whereas the second binding moieties are antigens.

According to still further features in the described preferred embodiments, the first situation is a human disease.

According to still further features in the described preferred embodiments, the first binding moieties and the second binding moieties are each independently selected from the group consisting of nucleic acids, proteins, carbohydrates and fatty acids.

According to yet another aspect of the present invention, there is provided a method of clustering a subset of antigens of a plurality of antigens, the subset of antigens being reactive with a plurality of antibodies being derived from a plurality of patients having an impaired immune system and suffering from a disease, the method comprising the steps of (a) assaying binding of the plurality of antibodies being derived from the plurality of patients with the plurality of antigens; (b) assaying binding of a plurality of antibodies being derived from a plurality of individuals free of the disease with the plurality of antigens; and (c) clustering the subset of antigens being reactive with the plurality of antibodies being derived from the plurality of patients having the impaired immune system and suffering from the disease.

According to this aspect of the present invention, there is also provided a system for clustering a subset of antigens of a plurality of antigens, the subset of antigens being reactive with a plurality of antibodies being derived from a plurality of patients having an impaired immune system and suffering from a disease, the system comprising a data acquisition device and a computation device communicating therewith, the data acquisition device and the computation device being designed, constructed and configured for (a) assaying binding of the plurality of antibodies being derived from the plurality of patients with the plurality of antigens; (b) assaying binding of a plurality of antibodies being derived from a plurality of individuals free of the disease with the plurality of antigens; and (c) clustering the subset of antigens being reactive with the plurality of antibodies being derived from the plurality of patients having the impaired immune system and suffering from the disease.

According to still another aspect of the present invention, there is provided a method of diagnosing a disease of a subject, the method comprising the steps of (a) clustering a subset of antigens of a plurality of antigens, the subset of antigens being reactive with a plurality of antibodies being derived from a plurality of patients having an impaired immune system and suffering from the disease by (i) assaying binding of the plurality of antibodies being derived from the plurality of patients with the plurality of antigens; (ii) assaying binding of a plurality of antibodies being derived from a plurality of individuals free of the disease with the plurality of antigens; and (iii) clustering the subset of antigens being reactive with the plurality of antibodies being derived from the plurality of patients having the impaired immune system and suffering from the disease; and (b) associating or deassociating serum of the subject with a cluster resulting from step (a)(iii).

According to this aspect of the present invention, there is also provided a system for diagnosing a disease of a subject, the system comprising a data acquisition device and a computation device communicating therewith, the data acquisition device and the computation device being designed, constructed and configured for (a) clustering a subset of antigens of a plurality of antigens, the subset of antigens being reactive with a plurality of antibodies being derived from a plurality of patients having an impaired immune system and suffering from the disease by (i) assaying binding of the plurality of antibodies being derived from the plurality of patients with the plurality of antigens; (ii) assaying binding of a plurality of antibodies being derived from a plurality of individuals free of the disease with the plurality of antigens; and (iii) clustering the subset of antigens being reactive with the plurality of antibodies being derived from the plurality of patients having the impaired immune system and suffering from the disease; and (b) associating or deassociating serum of the subject with a cluster resulting from step (a)(iii).

According to yet an additional aspect of the present invention there is provided an article of manufacture comprising a surface and antigens being arranged on the surface, each in an independent addressable location, the antigens including a plurality of subsets of antigens, each of the plurality of subsets of antigens being selected by a method of clustering a subset of antigens of a plurality of antigens, the subset of antigens being reactive with a plurality of antibodies being derived from a plurality of patients having an impaired immune system and suffering from a specific disease, the method being effected by (a) assaying binding of the plurality of antibodies being derived from the plurality of patients with the plurality of antigens; (b) assaying binding of a plurality of antibodies being derived from a plurality of individuals free of the disease with the plurality of antigens; and (c) clustering the subset of antigens being reactive with the plurality of antibodies being derived from the plurality of patients having the impaired immune system and suffering from the disease.

According to further features in preferred embodiments of the invention described below, the step of clustering is effected so as to include in the subset of antigens those antigens for which the patients and individuals best decompose into clusters according to a known clinical diagnosis of the patients and individuals.

According to still further features in the described preferred embodiments, the step of clustering is effected by a supervised classifier.

According to still further features in the described preferred embodiments, the supervised classifier is a neural network algorithm.

According to still further features in the described preferred embodiments, the step of clustering is effected by a unsupervised classifier.

According to still further features in the described preferred embodiments, the unsupervised classifier is a coupled two way clustering algorithm.

According to still further features in the described preferred embodiments, the step of clustering is effected so as to result in optimal sensitivity.

According to still further features in the described preferred embodiments, the step of clustering is effected so as to result in optimal specificity.

According to still further features in the described preferred embodiments, the step of clustering is effected so as to result in optimal specificity and optimal sensitivity.

According to still further features in the described preferred embodiments, the step of clustering is effected by (i) clustering the antibodies and the antigens and identifying all stable antibody and antigen clusters; (ii) scanning the antigen clusters, while using reactivity levels of antigens of each antigens cluster as a feature set representing first object sets containing either all of the antibodies or any of the stable antibody clusters; (iii) scanning the antibody clusters, while using reactivity levels of antibodies of each antibody cluster as a feature set representing second object sets containing either all of the antigens or any of the stable antigen clusters; (iv) tracking all antibody and antigen stable clusters thus generated; (v) repeating steps (i)-(iv) until no new antibody and antigen stable clusters being generated, thereby obtaining final stable antigens and antibody clusters and pointers identifying how all of the stable antibody and antigen clusters have been generated.

According to still further features in the described preferred embodiments the disease is selected from the group consisting of a autoimmune disease, a cancer, an immune deficiency disease, a degenerative disease, a metabolic disease, an infectious disease, a genetic disease, a mental disorder, an organ transplantation, an injury or an intoxication, or any condition involving cytokines or inflammation.

According to still further features in the described preferred embodiments, the autoimmune disease is selected from the group consisting of ankylosing spondylitis, uveitis, Goodpasture's syndrome, multiple sclerosis, Grave's disease, myasthenia gravis, systemic lupus erythematosus, systemic sclerosis, mixed connective tissue disease, dermatitis herpetiformis, celiac disease, ulcerative colitis, Crohn's disease, chronic active hepatitis, endometriosis, ulcerative colitis, insulin-dependent diabetes mellitus, psoriasis, pemphingus vulgaris, Hashimoto's thyroiditis, rheumatoid arthritis, idiopathic thrombocytopenic purpura, Sjogren's syndrome, uveroretinitis, autoimmune hemolytic anemia, vitiligo, primary biliary cirrhosis, inflammatory bowel disease, Bechet's disease, auricular chondritis, tympanosclerosis, autoimmune salpingitis, otosclerosis, secretory otitis media, necrotizing otitis media, autoimmune sensorineural hearing loss, Meniere's disease and cochlear vasculitis.

The present invention successfully addresses the shortcomings of the presently known configurations by opening new horizons in the ability to monitor changes in the immune system in cases of pathologies such as autoimmune diseases and immune deficiencies and as a response to treatment, such as a radiotherapy and/or chemotherapy treatment or immune depressant therapy or specific immune modulation.

Implementation of the methods and systems of the present invention involves performing or completing selected tasks or steps manually, automatically, or a combination thereof. Moreover, according to actual instrumentation and equipment of preferred embodiments of the methods and systems of the present invention, several selected steps could be implemented by hardware or by software on any operating system of any firmware or a combination thereof. For example, as hardware, selected steps of the invention could be implemented as an electronic chip or a circuit. As software, selected steps of the invention could be implemented as a plurality of software instructions being executed by a computer using any suitable operating system. In any case, selected steps of the methods of the invention could be described as being performed by a data processor, such as a computing platform (computation device) for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
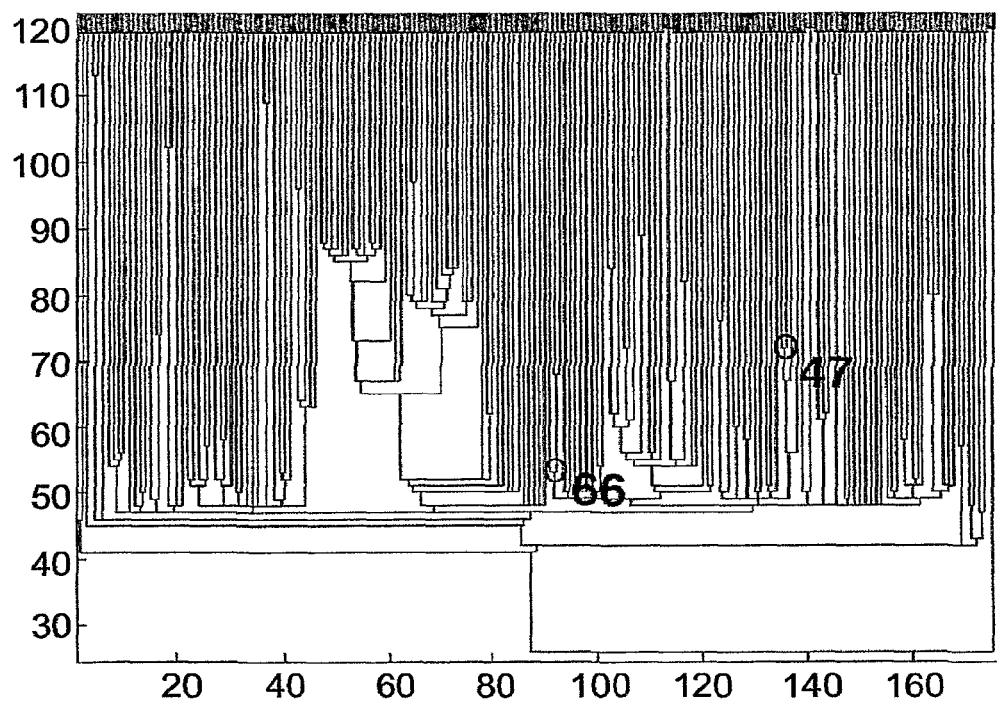
FIG. 1 is a dendrogram of antigens, created by clustering all antigens using the full set of subjects. Each junction represents the breaking of a cluster into two smaller clusters. Two Clusters which are used for analysis of specific subject populations are labeled by the corresponding cluster number. The individual antigens of each of these clusters are colored as follows: cluster 66-white; cluster 47-gray.

The present invention is of a method, system and an article of manufacture which can be used for clustering and thereby identifying predefined binding moieties of a one type reactive with undetermined binding moieties of a second type. Particularly, the present invention can be used for clustering and thereby identifying predefined antigens reactive with undetermined immunoglobulins of antibodies derived from patient subjects with an impaired immune system.

As used herein in the specification and in the claims section that follows, the phrase "impaired immune system" refers to an immune system characterized by an abnormal activity, either over activity as a result of, for example, an autoimmune disease, infection or inflammation, or under activity as a result of, for example, an immune deficiency disease, chemotherapy, radiotherapy or the use of immune depressants. The abnormal activity of the impaired immune system can also be the result of, or reflect, cancer, degenerative disease, metabolic disease, reaction to transplantation, trauma, mental disorder, intoxication, or genetic disease.

It should also be understood that patterns of antibody reactivities are not limited to those present in serum antibodies, but antibodies may also be measured in whole blood or blood plasma, or in other body fluids such as saliva, intestinal secretions or urine, or in any other compartment in which antibodies are found.

It should also be understood that antibody patterns for the present purpose may be detected using peptide libraries or organic synthetic compounds, as well as conventional antigens, as have been outlined here. An antigen is defined as any molecule that can be bound by the antigen-combining site of an antibody or T-cell receptor molecule; therefore, various classes or types of molecular species can be used to detect antibody patterns, provided that the molecules can interact with specific antibodies.

Before explaining at least one embodiment of the invention in detail, it is to be understood that the invention is not limited in its application to the details of construction and the arrangement of the components set forth in the following description or illustrated in the drawings or exemplified by the examples. The invention is capable of other embodiments or of being practiced or carried out in various ways. Also, it is to be understood that the phraseology and terminology employed herein is for the purpose of description and should not be regarded as limiting.

Thus, according to one aspect of the present invention there is provided a method of classifying into a predefined first situation (such as a human disease, e.g., an autoimmune disease) of at least two distinct situations (such as an autoimmune disease, healthy, and another autoimmune disease) a binding pattern of a plurality of undetermined first binding moieties (such as serum immunoglobulins) to a predefined set of a plurality of potential second binding moieties (such as a predetermined set or sets of antigens. The plurality of undetermined first binding moieties according to this aspect of the invention are derived from a first group of objects (e.g., patients) which are associated with the predefined first situation (e.g., the autoimmune disease) and from at least one second group of objects (e.g., healthy individuals) which are associated with a situation other than the first situation (e.g., are free of the autoimmune disease).

The method according to this aspect of the present invention is effected by implementing the following method steps, in which, in a first step the plurality of undetermined first binding moieties of the first group of objects are assayed for binding to each of the plurality of potential second binding moieties. In a second step, which can precede, proceed or be simultaneous to the first step, the plurality of undetermined first binding moieties of the at least one second group of objects are assayed for binding to each of the plurality of potential second binding moieties. Finally, at least some of the plurality of potential second binding moieties are clustered into clusters of second binding moieties which bind first binding moieties of the undetermined first binding moieties from the first group of objects. Thereby, achieving the above classification, or, in other words, classifying into the predefined first situation the binding pattern of the plurality of undetermined first binding moieties of the objects being associated with the predefined first situation to the predefined set of the plurality of potential second binding moieties.

Figure 10:
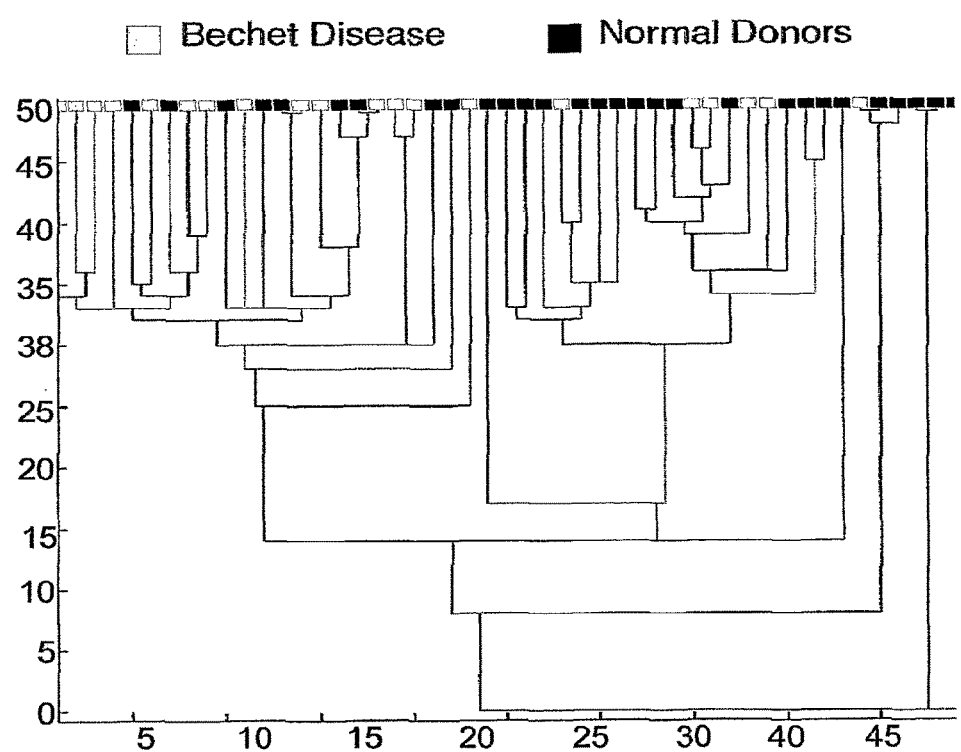
FIG. 10 is a dendogram created by clustering the Bechet Disease samples and the healthy serum samples using antigen cluster 13.

According to this aspect of the present invention there is also provided a system for classifying into a predefined first situation of at least two distinct situations, a binding pattern of a plurality of undetermined first binding moieties, to a predefined set of a plurality of potential second binding moieties. FIG. 10 provides a schematic representation of a system in accordance with the teachings of the present invention, which is referred to hereinbelow as system 20. System 20 includes a data acquisition device 22 and a computation device 24 communicating therewith. Depending on the strategy selected for monitoring binding, device 22 may, for example, be an electro-optical device capable of collecting optical data from an analyzed sample 25, such as, but not limited to a CCD, and may therefore be coupled to an optical magnification mechanism such as a microscope 26 or, in the alternative, device 22 may be a radioactive monitor having, either spatial resolution or matrix scanning capabilities. Besides communicating with device 22, computation device 24 preferably also communicates with a display device 28 which may serve for presentation of either raw data collected by data acquisition device 22 or the results of the analysis thereof. In any case, the data acquisition device and the computation device are designed, constructed and configured to serve for (a) assaying the plurality of undetermined first binding moieties of the first group of objects for binding to each of the plurality of potential second binding moieties; (b) assaying the plurality of undetermined first binding moieties of the at least one second group of objects for binding to each of the plurality of potential second binding moieties; and (c) clustering at least some of the plurality of potential second binding moieties into clusters of second binding moieties which bind first binding moieties of the undetermined first binding moieties from the first group of objects, thereby classifying into the predefined first situation the binding pattern of the plurality of undetermined first binding moieties of the objects which are associated with the predefined first situation to the predefined set of the plurality of potential second binding moieties.

According to another aspect of the present invention there is provided a method of classifying a specific object into a situation of at least two distinct situations. The method according to this aspect of the present invention is effected by implementing the following method steps, in which, in a first step, binding patterns of a plurality of undetermined first binding moieties, the plurality of undetermined first binding moieties are derived from a first group of objects which are associated with a predefined first situation of at least two distinct situations, and from at least one second group of objects which are associated with a situation other than the first situation of the at least two distinct situations, are classified into a predefined set of a plurality of potential second binding moieties by clustering at least some of the plurality of potential second binding moieties into a cluster of second binding moieties which bind first binding moieties of the undetermined first binding moieties from the first group of objects. Then, the cluster is used for determining whether the specific object is classifiable into the situation of the at least two distinct situations.

According to this aspect of the present invention there is also provided a system for classifying a specific object into a situation of at least two distinct situations. The system includes a data acquisition device and a computation device communicating therewith essentially as described above. The data acquisition device and the computation device are designed, constructed and configured for (a) classifying binding patterns of a plurality of undetermined first binding moieties, the plurality of undetermined first binding moieties are derived from a first group of objects which are associated with a predefined first situation of at least two distinct situations, and from at least one second group of objects which are associated with a situation other than the first situation of the at least two distinct situations, into a predefined set of a plurality of potential second binding moieties by clustering at least some of the plurality of potential second binding moieties into a cluster of second binding moieties which bind first binding moieties of the undetermined first binding moieties from the first group of objects; and (b) using the cluster for determining whether the specific object is classifiable into the situation of the at least two distinct situations.

According to a preferred embodiment of the described aspects of the invention, clustering at least some of the plurality of potential second binding moieties into clusters of second binding moieties which bind first binding moieties of the undetermined first binding moieties from the first group of objects is effected by a supervised classifier, such as a neural network algorithm, or, preferably, by a unsupervised classifier, as is further exemplified in the Examples section that follows with respect to antibodies present in sera or other body fluids or secretions of autoimmune disease patients and known antigens. As is further elaborated, exemplified and reasoned in the examples section below, the unsupervised classifier is, according to a presently preferred embodiment of the invention, a coupled two way clustering algorithm.

According to another preferred embodiment of the present invention, the described methods further include a step of scanning the second binding moieties which bind first binding moieties of the undetermined first binding moieties from the first group of objects and selecting for a subset of the second binding moieties resulting in an optimal sensitivity and/or optimal specificity.

The first and second binding moieties can be of any biological or chemical type which are capable of stable and monitorable interaction. such moieties include, but are not limited to, nucleic acids (e.g., DNA or RNA), proteins (e.g., antigens and antibodies), carbohydrates, fatty acids, peptides, peptide libraries, organic compounds or tissue extracts. Mixed moieties may also find uses, e.g., glycoproteins or acylated proteins. Such binding moieties can be derived from commercial sources, biological sources or may be synthesized, produced in or purchased from specialized laboratories.

The situations according to the present invention may include, for example, medical situations of human beings or animals, different subtraction libraries, different display libraries, and the like. A human disease can be for example an autoimmune disease, a cancer and an immune deficiency disease (which may, for example, be due to viral infection or treatment with immune depressants). The autoimmune disease can be, for example, ankylosing spondylitis, uveitis, Goodpasture's syndrome, multiple sclerosis, Grave's disease, myasthenia gravis, systemic lupus erythematosus, systemic sclerosis, mixed connective tissue disease, dermatitis herpetiformis, celiac disease, ulcerative colitis, Crohn's disease, chronic active hepatitis, endometriosis, ulcerative colitis, insulin-dependent diabetes mellitus, psoriasis, pemphingus vulgaris, Hashimoto's thyroiditis, rheumatoid arthritis, idiopathic thrombocytopenic purpura, Sjogren's syndrome, uveroretinitis, autoimmune hemolytic anemia, vitiligo, primary biliary cirrhosis, inflammatory bowel disease, Bechet's disease, auricular chondritis, tympanosclerosis, autoimmune salpingitis, otosclerosis, secretory otitis media, necrotizing otitis media, autoimmune sensorineural hearing loss, Meniere's disease and cochlear vasculitis. However, the invention described herein could also be applied to conditions like, a degenerative disease, a metabolic disease, an infectious disease, a genetic disease, a mental disorder, an organ transplantation, an injury or an intoxication, or any condition involving cytokines or inflammation.

According to yet another aspect of the present invention there is provided a method of clustering a subset of antigens of a plurality of antigens, the subset of antigens are reactive with a plurality of antibodies derived from a plurality of patients having an impaired immune system and suffering from a disease. The method according to this aspect of the present invention is effected by implementing the following method steps, in which, in a first step, binding of the plurality of antibodies derived from the plurality of patients with the plurality of antigens is assayed. In a second step of the method according to this aspect of the present invention, binding of a plurality of antibodies being derived from a plurality of individuals free of the disease with the plurality of antigens is assayed. Finally, the subset of antigens which are reactive with the plurality of antibodies derived from the plurality of patients having the impaired immune system and suffering from the disease are clustered into a cluster.

According to this aspect of the present invention, there is also provided a system for clustering a subset of antigens of a plurality of antigens. The system includes a data acquisition device and a computation device communicating therewith. The data acquisition device and the computation device are designed, constructed and configured for (a) assaying binding of the plurality of antibodies being derived from the plurality of patients with the plurality of antigens; (b) assaying binding of a plurality of antibodies being derived from a plurality of individuals free of the disease with the plurality of antigens; and (c) clustering the subset of antigens being reactive with the plurality of antibodies derived from the plurality of patients having the impaired immune system and suffering from the disease.

According to still another aspect of the present invention, there is provided a method of diagnosing a disease of a subject. The method according to this aspect of the present invention is effected by implementing the following method steps, in which, in a first step, a subset of antigens of a plurality of antigens are clustered, the subset of antigens are reactive with a plurality of antibodies derived from a plurality of patients having an impaired immune system and suffering from the disease by (i) assaying binding of the plurality of antibodies derived from the plurality of patients with the plurality of antigens; (ii) assaying binding of a plurality of antibodies derived from a plurality of individuals free of the disease with the plurality of antigens; and (iii) clustering the subset of antigens which are reactive with the plurality of antibodies derived from the plurality of patients having the impaired immune system and suffering from the disease. Then, serum of the subject is associated or disassociated with a cluster resulting from step (a)(iii).

According to this aspect of the present invention, there is also provided a system for diagnosing a disease of a subject. The system includes a data acquisition device and a computation device communicating therewith. The data acquisition device and the computation device are designed, constructed and configured for (a) clustering a subset of antigens of a plurality of antigens, the subset of antigens are reactive with a plurality of antibodies derived from a plurality of patients having an impaired immune system and suffering from the disease by (i) assaying binding of the plurality of antibodies derived from the plurality of patients with the plurality of antigens; (ii) assaying binding of a plurality of antibodies derived from a plurality of individuals free of the disease with the plurality of antigens; and (iii) clustering the subset of antigens which are reactive with the plurality of antibodies derived from the plurality of patients having the impaired immune system and suffering from the disease; and (b) associating or deassociating serum of the subject with a cluster resulting from step (a)(iii).

According to an additional aspect of the present invention, there is provided an article of manufacture comprising a surface and antigens being arranged on the surface, each in an independent addressable location, the antigens including a subset of antigens being selected by a method of clustering the subset of antigens of a plurality of antigens, the subset of antigens being reactive with a plurality of antibodies being derived from a plurality of patients having an impaired immune system and suffering from a disease, the method being effected by (a) assaying binding of the plurality of antibodies derived from the plurality of patients with the plurality of antigens; (b) assaying binding of a plurality of antibodies derived from a plurality of individuals free of the disease with the plurality of antigens; and (c) clustering the subset of antigens being reactive with the plurality of antibodies derived from the plurality of patients having the impaired immune system and suffering from the disease.

According to yet an additional aspect of the present invention, there is provided an article of manufacture comprising a surface and antigens being arranged on the surface, each in an independent addressable location, the antigens including a plurality of subsets of antigens, each of the plurality of subsets of antigens being selected by a method of clustering a subset of antigens of a plurality of antigens, the subset of antigens being reactive with a plurality of antibodies derived from a plurality of patients having an impaired immune system and suffering from a specific disease, the method being effected by (a) assaying binding of the plurality of antibodies derived from the plurality of patients with the plurality of antigens; (b) assaying binding of a plurality of antibodies derived from a plurality of individuals free of the disease with the plurality of antigens; and (c) clustering the subset of antigens being reactive with the plurality of antibodies derived from the plurality of patients having the impaired immune system and suffering from the disease.

According to a preferred embodiment of the invention, the step of clustering to the subset of antigens being reactive with the plurality of antibodies derived from the plurality of patients having the impaired immune system and suffering from the disease is effected so as to include in the subset of antigens those antigens for which the patients and individuals best decompose into clusters according to a known clinical diagnosis of the patients and individuals. Preferably, the step of clustering is effected by an unsupervised classifier, such as a coupled two way clustering algorithm. The step of clustering is preferably effected so as to result in optimal sensitivity and/or optimal specificity.

Still preferably, the step of clustering the subset of antigens being reactive with the plurality of antibodies derived from the plurality of patients having the impaired immune system and suffering from the disease is effected by (i) clustering the antibodies and the antigens and identifying all stable antibody and antigen clusters; (ii) scanning the antigen clusters, while using reactivity levels of antigens of each antigens cluster as a feature set representing first object sets containing either all of the antibodies or any of the stable antibody clusters; (iii) scanning the antibody clusters, while using reactivity levels of antibodies of each antibody cluster as a feature set representing second object sets containing either all of the antigens or any of the stable antigen clusters; (iv) tracking all antibody and antigen stable clusters thus generated; (v) repeating steps (i)-(iv) until no new antibody and antigen stable clusters being generated, thereby obtaining final stable antigens and antibody clusters and pointers identifying how all of the stable antibody and antigen clusters have been generated.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include immunological techniques. Such techniques are thoroughly explained in the literature. See, for example, "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Example 1

General Methodology

A general approach to global antibody analysis is described herein aimed to quantitatively assay the binding of patients' antibodies to a large number (tens to hundreds or thousands) of different antigens of human origin (self-antigens) or from other sources, or to libraries of antigens (e.g. expression libraries, peptide libraries, etc), and to analyze, using bio-informatic technology, the global pattern of the reactivities to selected groups of antigens. The bio-informatic process is done in two stages, as follows.

The first stage includes classification of the antibody patterns characteristic of particular diseases. To this end, sera are collected from healthy persons and from persons known to suffer form certain diseases, and the sera are then assayed for the presence of antibodies binding to the various test antigens. The assays described below were performed using standard ELISA techniques (see below), but the assay system can easily be miniaturized and made suitable for the types of automated technology now in use for genomic and proteinomic chips. To this end, see for example (15-18), which are incorporated herein by reference. Here an informatics computer program designed to select sets of antigens is described, which program actually clusters together the antibody patterns of patients with particular diseases and separate these persons by their antibody patterns from the antibody patterns of healthy persons and from those of patients with other diseases. The computer program described herein can scan the sets of antigens and antibodies and select those that provide the highest sensitivity (include the greatest number of persons with the disease) and the highest specificity (exclude the greatest numbers of persons with other diseases or no disease). In the field of cluster analysis, the biological term sensitivity is referred to as efficiency (E) and the term specificity is called purity (P). These terms will be used herein interchangeably. Thus the sets of particular antigens provide classifiers for a particular diseases.

The second stage involves the use of classifiers to test individual persons in need of diagnosis or theranosis. Once the recipe of antigens and reactivities have been established, the diagnosis of various diseases and the monitoring of the state of a subject's immune system are made according to the particular pattern classifiers. In other words, the fit of a patient's antibody pattern to a disease classifier reveals the disease or condition of interest.

Example 2

The Antigens

The antigens that were used according to the present invention to reveal the global patterns reactivities can be divided into different sets according, for example, to their origin. Different members of each set can be used in the tests. Table 1 below provides a non-limiting example of antigens which can be used in accordance with the teachings of the present invention and which were used to reduce the present invention to practice, as is further detailed hereinunder.

TABLE 1

| Antigen Sets | | |
|---|---|---|
| Group | Function/Origin | Antigen |
| Cellular Structure | Cytoskeleton | Actin |
| | | Tubulin |
| | | Myosin |
| | | Tropomyosin |
| | | Vimentin |

TABLE 1-continued

Antigen Sets

| Group | Function/Origin | Antigen |
|---|---|---|
| | Extracellular matrix | Fibronectin |
| | | Acid Collagen |
| | | Collagen I |
| | | Collagen IX |
| | | Collagen VI |
| | | Collagen X |
| | | Heparin |
| | | Laminin |
| | | Collagenase |
| Cellular Membranes | Phospholipids | Cardiolipin |
| | | Glucocerebroside |
| | | Phosphoethanolamine |
| | | Cholesterol |
| Cellular Metabolism | Glucose | Enolase |
| | | Aldolase |
| | | Alkaline Phosphatase |
| | Apoptosis | Annexin 33 kDa. |
| | | Annexin 67 kDa. |
| | Monooxigenases | Cytochrome P450-C |
| | | Catalase |
| | | Peroxidase |
| | | Tyrosinase |
| | Others | Ribonuclease |
| Nucleus | Protein | Histone II A |
| | DNA | Double Stranded DNA |
| | | Single Stranded DNA |
| | Synthetic Oligomers | Poly C |
| | | Poly A |
| | | Poly T |
| | | Poly G |
| | | Poly ATA |
| | | Poly TAT |
| Plasma proteins | Carriers | Holo-Transferrin |
| | | Albumin (human) |
| | | Albumin (bovine) |
| | | Albumin (chicken) |
| | | Fetuin (bovine) |
| | Coagulation | Factor II |
| | | Factor VII |
| | | Fibrinogen |
| | | Fibrin |
| | Complement | C1 |
| | | C1q |
| Immune System | Immunoglobulins | Human IgG |
| | | Human IgM |
| | Monoclonal Antibodies | P277 F(ab)2 |
| | T Cell Receptors | C9 |
| | | N4 |
| | Cytokines and Chemokines | Interleukin 2 |
| | | Interleukin 10 |
| | | Interleukin 4 |
| | | Interferon-□ |
| Tissue Antigens | Heat Shock Proteins and peptides | Heat Shock Protein 60 |
| | | p277 |
| | | Ec27 |
| | | p278 |
| | Islet Antigens | GAD |
| | | Insulin |
| | CNS | Brain Extract |
| | | Human MOG |
| | | Mouse MOG |
| | | MOG 94-111 |
| | | MOG 35-55 |
| | | MBP |
| | Muscle and skeleton | Acetylcholine Receptor |
| | | Cartilage Extract |
| | | Myoglobulin |
| | Thyroid | Thyroglobulin |
| | Blood cells and platelets | Hemoglobin A |
| | | Spectrin |
| | Proteins | TB PPD |
| | | Glutathion S |
| | | KLH |
| | Peptides | Pepstatin |
| | | R13 |
| | Others | LPS |

Example 3

Immunological Methods

ELISA plates, 96 well, (Nalge Nunc International) are coated by incubation of the desired antigens dissolved in basic carbonate buffer pH 9.6, for 2 hours at 37° C., followed by an overnight incubation at 4° C. The plates are then washed with PBS Tween 0.05% (PBST), and blocked for 2 hours with BSA 3% at 37° C. The sera for analysis are then added at a dilution of 1:100 in BSA 0.3%. After 3 hours of incubation at 37° C., the sera are removed and the plates are washed with PBST. Bound antibodies are detected with an alkaline phosphatase conjugated antibody (Jackson ImmunoResearch Labs. Inc.) that recognizes both human IgG and IgM, incubated for 1.5 hours in a 1:1500 dilution in BSA 0.3% at 37° C. After washing with PBS, the alkaline phosphatase substrate (Sigma) is added at 0.5 mg/ml dissolved in diethanolamine buffer, and the OD at 405 nm is determined after 30 and 60 minutes of incubation at 37° C. Once the readings at 405 nm were done, the plates were washed 5 times with PBST and incubated for 1 hour at 37° C. with a horseradish peroxidase conjugated antibody (Jackson ImmunoResearch Labs. Inc.) that recognizes human IgM, in a 1:1500 dilution in BSA 0.3%. After washing with PBS, the horseradish substrate (Sigma) was added, and the OD at 405 nm was determined after 30 and 60 minutes of incubation at 37° C.

Example 4

Rational of Data Presentation and Processing

In the examples that follow, the above ELISA procedure was applied for the analysis of the antibody reactivities of a group of N=40 serum samples against a panel of M=88 different antigens, and the results (readings of OD at 405 nm), were placed in a matrix A, whose element $A_j^i$ represents the extent to which the serum of subject i reacts with antigen test j, j=1 ... 176. The first 88 rows, j=1 ... 88, correspond to IgM levels in sera, while the last 88 rows, j=89 ... 176, correspond to levels of IgG plus IgM in sera.

The "immune state" of subject i is represented by vector $\vec{A^i}$ (which is composed of 176 components). The entire set of subjects is represented by 40 such vectors. Similarly, antigen j is represented by the (40 component) vector $\vec{A_j}$. The set of antigen tests were represented by 176 such vectors.

The aim was to classify the subjects, on the basis of the reaction patterns of the sera with the antigens, according to their known diagnosis, as healthy versus diseased. In this example, the number of datapoints (the subjects) is about the same as the dimension of the space in which they are represented (the antigens). Therefore, it is most likely that a classifier that accomplishes this task can be found constructed in a supervised way according to preconceived categories. Such a classifier, however, would most likely run into problems of overtraining and have a low generalization ability.

To obtain the best results, one should therefore perform an unsupervised exploratory analysis of the data, identify natural classes or clusters that exist in it, and then check whether any of these natural clusters contains predominantly subjects with a particular diagnosis. Once the underlying structure has been revealed by an unsupervised method, one can construct classifiers in a modular supervised manner, to identify the various classes present in the data.

Hence the aim was to carry out an unsupervised exploratory investigation of to the underlying structure of the two sets of vectors mentioned above. In particular answers to the following questions were sought for:
1. Does the set of subjects, as represented by the vectors $\vec{A^i}$, decompose into clusters according to the known clinical diagnosis?
2. Do the antigens form clusters with correlated activities?
3. What additional information can be obtained by a two-way clustering procedure, using clusters of antigens to classify the sera?
4. Can one identify antigens that are particularly suited to answer specific questions about the status of the subjects?

As is further demonstrated hereinbelow, positive answers were obtained for the above four questions.

Example 5

Normalization

Sera taken from different subjects may have different concentrations, introducing an overall bias which varies from subject to subject. This bias is considered as a multiplicative factor. To eliminate it, $\vec{A^i}$ subject i was represented by vector $\vec{T^i}$, whose elements are:

$$T^i_j = \frac{M}{\sum_k \log A^i_k} \cdot \log A^i_j \qquad (1)$$

This normalization is only done once, for the full matrix. There is no reason to renormalize the columns when only a subgroup of the antigens is taken. This way, each coordinate still represents the measurement in relation to the common baseline in the case of subjects.

It is desired to identify clusters of antigens that relate to the same biological mechanism. If the reactivity expression profiles for antigens 1 and 2 are highly correlated, or highly anti-correlated, this may suggest that the antibodies that react with the two antigens belong to the same biological mechanism and therefore one wishes to cluster these two antigens together. Thus, each time one uses a submatrix of T, one renormalizes its rows to have mean 0, and variance 1. Denote the matrix with the renormalized rows as G.

The distance ($D_{i,k}$) between subjects i and k is the Euclidian distance:

$$D_{i,k} = \sqrt{\sum_j (G^i_j - G^k_j)^2} \qquad (2)$$

The distance ($d_{j,l}$) between two antigens j and l is taken as:

$$d_{j,l} = 1 - c^2_{j,l} = 1 - \sum_i (G^i_j - G^i_l)^2 \qquad (3)$$

where $c_{j,l}$ is the correlation between two antigen vectors ($-1 \leq c_{j,l} \leq 1$). This distance measure will be high if the antigens are correlated or anti-correlated, and low if they have no statistical dependence.

Example 6

Quality of Partition

A cluster that is clearly separated from the rest of the datapoints, can be identified, with high likelihood, by a supervised classifier (such as a trained neural network). To identify clusters of sera that are useful to a particular aim, such as identifying type 1 diabetics (hereinafter D1), the known labels of the subjects were used, producing a score that reflects the quality of a cluster of sera for the particular task of interest.

It should be emphasized that the known clinical labels are used only to evaluate the results, not to produce them.

An optimal solution of the task mentioned above is provided by a cluster of sera that contains all the D1 subjects and none of the others. Denoting the set of sera in this cluster by C, the set of all D1 patients by D1 and the size of each set (the number of sera in it) by |C| and |D/1|, respectively, one can define two figures of merit to measure the success of cluster C for our classification task: purity, P and efficiency, E, given by:

$$P = \frac{|C \cap D1|}{|C|}; E = \frac{|C \cap D1|}{|D1|} \qquad (4)$$

Example 7

Clustering Methodology

Clustering techniques are used according to the present invention to explore the structure of the data (15-17), that is, to reveal the natural classes present in it. This way one avoids introducing preconceived notions and biases about the existence of various partitions, and uncover those partitions that are indeed present. Such methods of partitioning data are unsupervised.

It is important to emphasize that the clustering algorithm does not make any use of the known clinical classification of the subjects.

A novel clustering algorithm, known as SPC (18, 19), which is based on ideas adopted from statistical mechanics of disordered ferromagnets was used herein. This algorithm uses the vectors mentioned above as its input. In general, N objects are clustered on the basis of the D dimensional vectors that represent them. The D quantities that constitute the components of such a vector are called the set of features that were used to represent the objects.

For example, to cluster the antigens (M=176 objects), one uses their normalized reactivities with all the sera, $\vec{G}_j'$, j=1, 2, ... 82, as the set of features. The output of the algorithm is in the form of a dendrogram, as is shown in FIG. 1. The vertical axis of this dendrogram represents the resolution, controlled by a parameter T, at which the datapoints are viewed. T=0 corresponds to the lowest resolution, at which all datapoints are assigned to the same cluster. As T increases, groups of highly correlated antigens split off and form their own clusters, until finally one is left, at the highest resolutions, with 82 clusters (with a single antigen in each). The vertical position of the "stem" of each cluster indicates the value of T at which it appeared first (i.e., split off a larger "parent" cluster), as T was increased. Its horizontal position can be used as an indication of its proximity (in terms of similarity of expression patterns) to antigen clusters that have split from the same parent.

When one clusters the sera, one obtains a dendrogram, that starts, at T=0, with all subjects in one cluster, until each subject forms his or her own cluster.

The anti-antigen (or antibody) reactivities data presented above are fairly special in that it makes good sense to perform clustering analysis in two ways. The first views the $n_s$=40 sera as the N=$n_s$ objects to be clustered, with the $n_g$=176 anti-antigen reactivities with a particular serum playing the role of the features, representing the corresponding subject as a point in a D=$n_g$ dimensional space.

The different "immune states" emerge from grouping together sera with similar or related antibody expression profiles. The other, not less natural way, looks for clusters of antigens that react correlatively with the different sera. This view considers the N=$n_g$ antigens as the objects to be clustered, each represented by its reactivity profile, as measured over all the sera, as a point in a D=$n_s$ dimensional space.

This clustering method, SPC, is used in conjunction with a recently developed Coupled Two Way Clustering (CTWC) (20, 21) approach, as is further detailed hereinunder.

Example 8

Coupled Two Way Clustering

The philosophy behind Coupled Two Way Clustering is to narrow down both the features that one uses and the data points that are clustered. Possibly, only a small subset of the antigens participate in a particular process of interest, which takes place only in a subset of the sera; by focusing on small subsets, one lowers the noise induced by the other sera and antigens. One looks for pairs of a relatively small subset F of features (either antigens or sera) and of objects O, (sera or antigens), such that when the set O is clustered using the features F, stable and significant partitions are obtained. Finding such pairs of subsets is a rather complex mathematical problem; the CTWC method produces such pairs in an iterative clustering process.

One starts with clustering the sera and the antigens of the full data set and identify all stable clusters of either sera or antigens. One, then scans these clusters one by one. The reactivity levels of the antigens of each cluster are used as the feature set F to represent object sets O. The different object sets O contain either all the sera or any cluster (which contains a subset of the sera). Similarly, one scans all stable clusters of sera and use them as the feature set F to identify stable clusters of antigens.

One keeps track of all the stable clusters that are generated, of both antigens, denoted as $v^g$, and sera $v^s$. The antigen and sera clusters are accumulated in antigen and sera lists, $V^g$ and $V^s$, respectively. Furthermore, one keeps all the chain of clustering analyses that has been performed (e.g., which subset was used as objects, which subset was used as features, and which were the stable clusters that have been identified).

When new clusters are found, one uses them in the next iteration. At each iteration step one clusters a subset of the objects (either sera or antigens) using a subset of the features (antigens or sera). The procedure stops when no new relevant information is generated. The outcome of the CTWC algorithm are the final sets $V^g$ and $V^s$ and the pointers that identify how all stable clusters of antigens and sera were generated.

Example 9

Summary of Data, Definitions and Notation

The clinical classifications and the subject indices corresponding to each are listed in Table 2. The color code used to designate each of these groups on the various dendrograms is indicated.

TABLE 2

| | Clinical Classifications | | | |
|---|---|---|---|---|
| label | Description | Indices | Color | Shape |
| D1 | Subjects with type 1 diabetes | 1-20 | black | triangle |
| NH | Normal healthy subjects | 21-40 | white | circle |

Example 10

Outline of the Analysis

The CTWC algorithm was started by using the full set of 40 sera as the feature set to cluster the full set of 176 antigen reactivities. The resulting dendrogram is shown in FIG. 1. The vertical axis is the temperature parameter T that controls the resolution. Stable antigen clusters were identified as those for which the interval between $T_c$, the value of T at which the cluster appears, and $T_d$, at which it disintegrates, is large. These clusters were recorded in the register $V^g$. In FIG. 1, those stable antigen clusters for which specific results are further shown below are numbered. The antigens of each of these clusters, and of other antigen groups that were used, are presented in Table 3 and 4 below.

TABLE 3

| | Antigen Cluster Description | | | | | |
|---|---|---|---|---|---|---|
| | Antigen | 66 | 14 | 47 | 5 | 26 |
| 2 | M Histone II A | | | | | X |
| 13 | M Lysine | | | | | X |
| 14 | M Arginine | | | | | X |
| 18 | M Cardiolipin | | X | | | |
| 25 | M Laminin | | | | | X |
| 30 | M Collagen X | | | | X | X |
| 37 | M Insulin | | | | X | |

TABLE 3-continued

Antigen Cluster Description

| | Antigen | 66 | 14 | 47 | 5 | 26 |
|---|---|---|---|---|---|---|
| 70 | M Fibrinogen | | | | | X |
| 85 | M Cartilage ext. | X | X | | | |
| 106 | GM Cardiolipin | X | | | | |
| 113 | GM Laminin | | | | | X |
| 117 | GM Collagen VII | | | | | X |
| 118 | GM Collagen X | | | | | X |
| 125 | GM Insulin | | | | X | |
| 140 | GM Adolase | | | | X | |
| 173 | GM Cartilage ext. | | X | | | |

The reactivities participating in each cluster are shown. The prefix GM or M indicates that the reactivity was detected with an anti IgM plus IgG or an anti IgM secondary antibody, respectively.

TABLE 4

Antigen Clusters Description

| | antigen | 9 | 13 | 18 | 19 |
|---|---|---|---|---|---|
| 1 | Actin | | | | X |
| 2 | Spectrin | | | | X |
| 3 | Myosin | | | | |
| 4 | Tropomiosin | | | | |
| 5 | Vimentin | | | | X |
| 6 | Tubulin | | | | |
| 7 | Fibronectin | | | | X |
| 8 | Collagen | | | | X |
| 9 | Collagen I | | | | X |
| 10 | Collagen IX | | | | X |
| 11 | Collagen VI | | | | |
| 12 | Collagen X | | | | |
| 13 | Heparin | | | X | |
| 14 | Laminin | | | | |
| 15 | Collagenase | | | | |
| 16 | Catalase | | X | | |
| 17 | Peroxidase | | | | X |
| 18 | Tyrosinase | | | | X |
| 19 | Enolase | | | | X |
| 20 | Aldolase | | | | |
| 21 | Alkaline Phos | | | | |
| 22 | Ribonuclease | | | | X |
| 23 | Annexin 33 | | | | |
| 24 | Annexin 67 | | | | |
| 25 | Cytochrome C | | | | |
| 26 | Hemoglobin A | | X | | |
| 27 | Mioglobulin | | X | | |
| 28 | H Albumin | | | | X |
| 29 | R Albumin | | | | X |
| 30 | O Albumin | | | | |
| 31 | Fetuin | | | | |
| 32 | Thyroglobulin | | | | |
| 33 | H Transferrin | | | | |
| 34 | Factor II | | | | |
| 35 | Factor VII | | | | |
| 36 | Fibrinogen | | | | |
| 37 | Fibrin | | | X | |
| 38 | C1 | | | | |
| 39 | C1q | | | | |
| 40 | H IgG | | | | |
| 41 | H IgM | | | | X |
| 42 | IL2 | | | | |
| 43 | IL10 | X | | | |
| 44 | IL4 | X | | | |
| 45 | IFN | | | | |
| 46 | GAD | | | | |
| 47 | Insulin | | X | | |
| 48 | HSP60 | | | | X |
| 49 | p277 | | | | X |
| 50 | anti P277 | | | | |
| 51 | C9 | | | | X |
| 52 | N4 | | | | X |
| 53 | Brain Ext | | | | X |
| 54 | Mouse MOG | | | | |
| 55 | RMOG 35 | | | | |
| 56 | Human MOG | | | | |
| 57 | HMOG 94 | | | | |
| 58 | R MBP | | | | |
| 59 | H AchR | | | | |
| 60 | Cartilage Ext | | | | |
| 61 | R13 | | | | |
| 62 | Pepstatin | | | | |
| 63 | Ec27 | | | | X |
| 64 | P278 | | | | X |
| 65 | GST | | | | |
| 66 | KLH | | | | X |
| 67 | LPS | | | | |
| 68 | TB PPD | | | | |
| 69 | Cardiolipin | | | | |
| 70 | Glucocereb | | | | X |
| 71 | Phosphoeth | | | | |
| 72 | Cholesterol | | | | |
| 73 | Histone II A | | | X | |
| 74 | DS DNA | | | | |
| 75 | SS DNA | | | X | |
| 76 | Poly C | | | X | |
| 77 | Poly A | | | X | |
| 78 | Poly T | | | X | |
| 79 | Poly G | | | X | |
| 80 | Poly ATA | | | X | |
| 81 | Poly TAT | | | X | |
| 82 | BLANK | | | | X |

For each registered antigen cluster $v^g$ (including the full group of antigens), the rows corresponding to the members of $v^g$ are taken out of the full matrix to form a submatrix. The columns of this submatrix are used to cluster the subjects, and stable clusters of subjects are registered in $V^s$.

In the following iterations, each registered cluster of subjects is clustered, using as the feature set the members of every registered cluster of antigens. Then, the antigen clusters are used as the objects and the different groups of sera as the features.

In each such iteration, the corresponding submatrix is used, with its rows renormalized. The resulting stable subject and antigen clusters are registered, and the process continues until no new stable clusters are found.

This algorithm has resulted in a list of registered clusters, of subjects and of antigens. From the list of subject clusters one chooses those with high purity and efficiency scores of the different classes of subjects (D1 and NH).

Experimental Results

Example 11

Separation of Diabetes from Healthy Subjects

Figure 2:
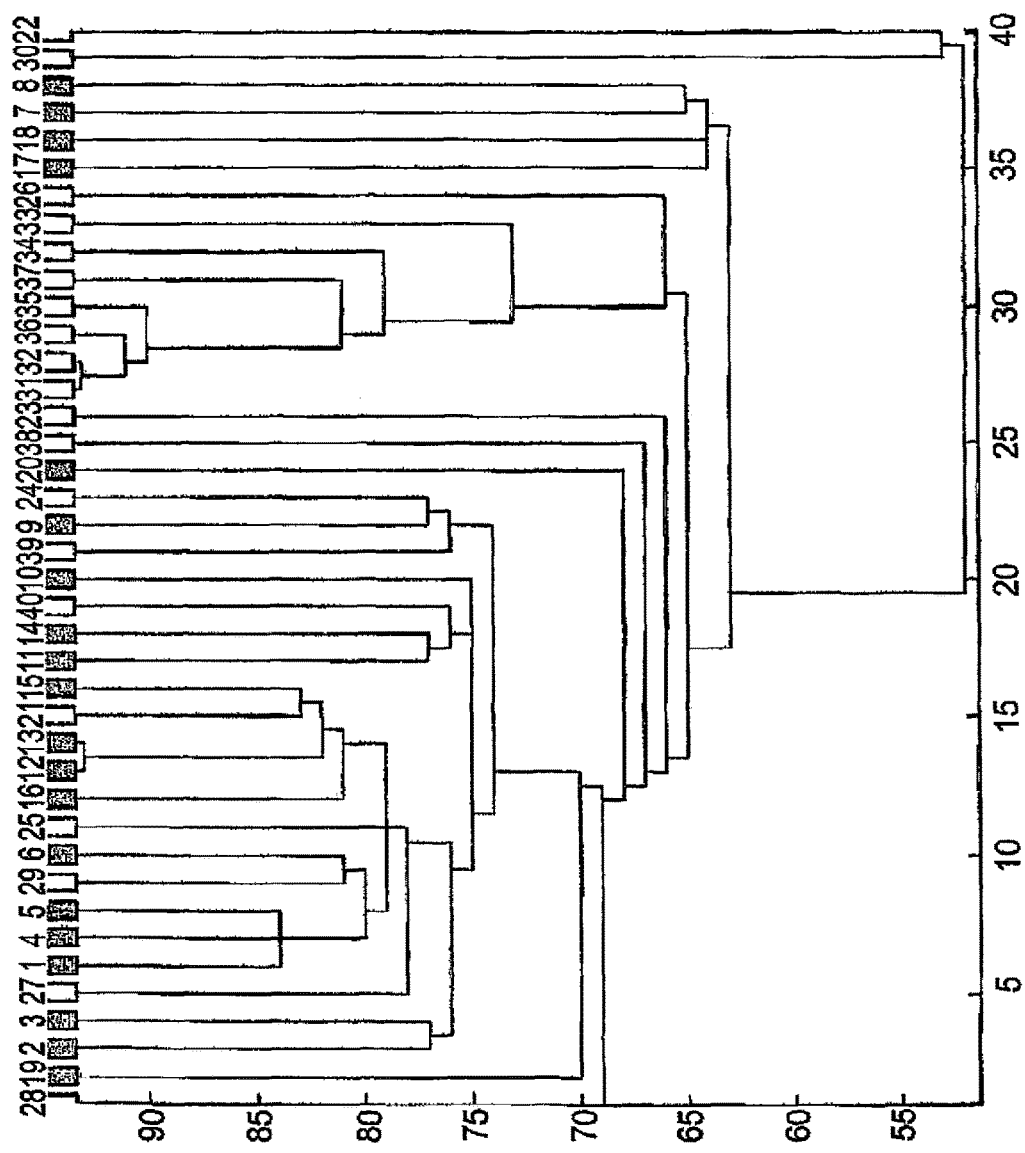
FIG. 2 is a dendrogram created by clustering all subjects, using the full set of antigens. Each leaf represents a subject. Diabetes subjects are colored black, and healthy ones—white.

To demonstrate the efficacy of the CTWC procedure, FIG. 2 presents the dendrogram obtained when all of the subjects I were clustered, using all antigens as the feature set. Indeed, one can observe a clear cluster of healthy subjects but it captures less then half of the NH subjects, and thus gives a poor classification.

Figure 3:
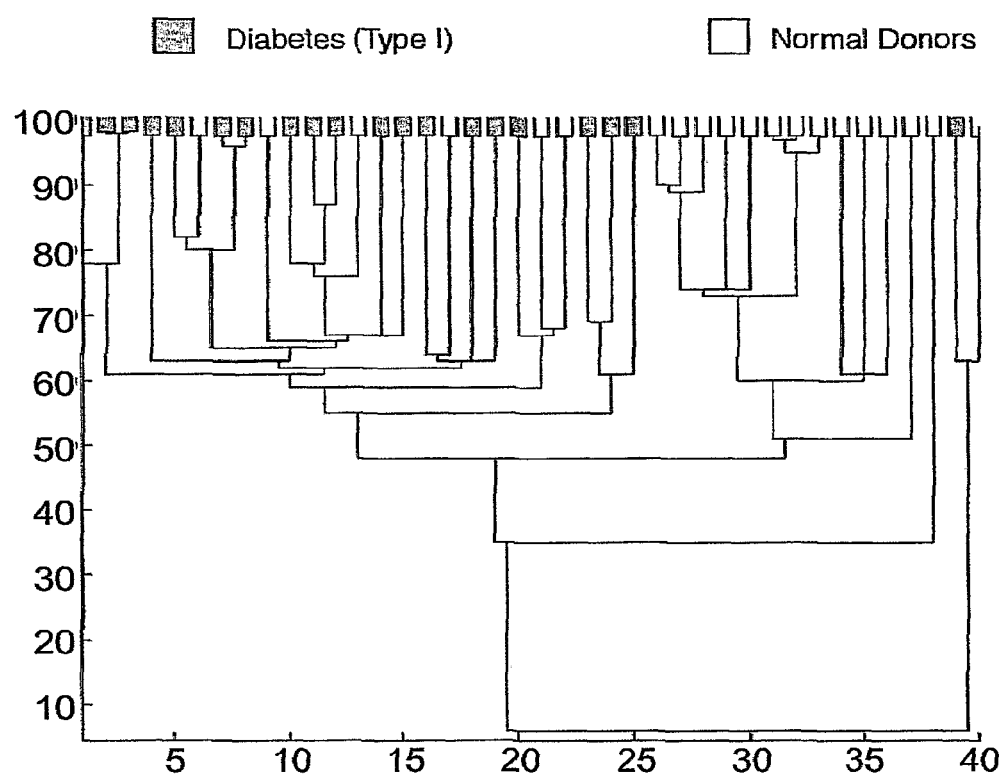
FIG. 3 is a subjects' dendrogram obtained by clustering the subjects, using the antigens of cluster 66. Leaf colors were assigned as in FIG. 2.

This is to be compared with the dendrogram of FIG. 3. Here the same subjects were clustered, using a particular antigen cluster (denoted as 66 in FIG. 1) as the feature set. A stable cluster of 11 healthy subjects was identified. A classifier which isolates this cluster and diagnoses all sera outside it as diseased will have purity of P=20/29=0.69 and efficiency of E=20/20=1.

Figure 5:
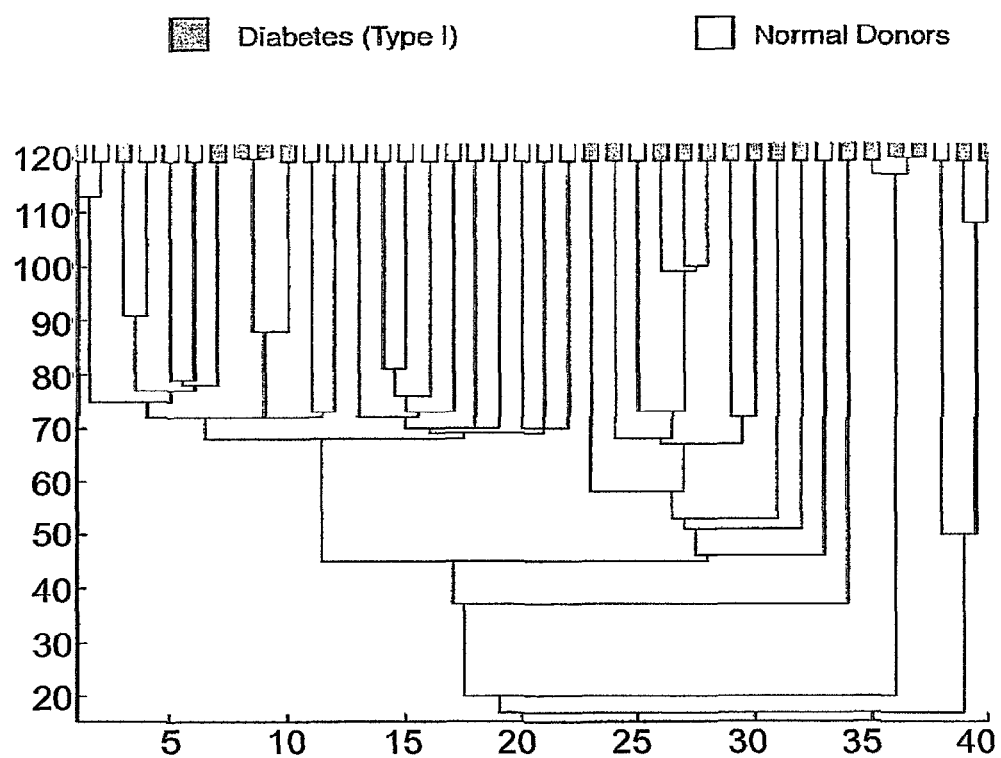
FIG. 5 is a dendrogram created by clustering the subjects, using cluster 5. Leaf colors—as in FIG. 2. The cluster that contains predominantly healthy subjects is marked by N.
Figure 6:
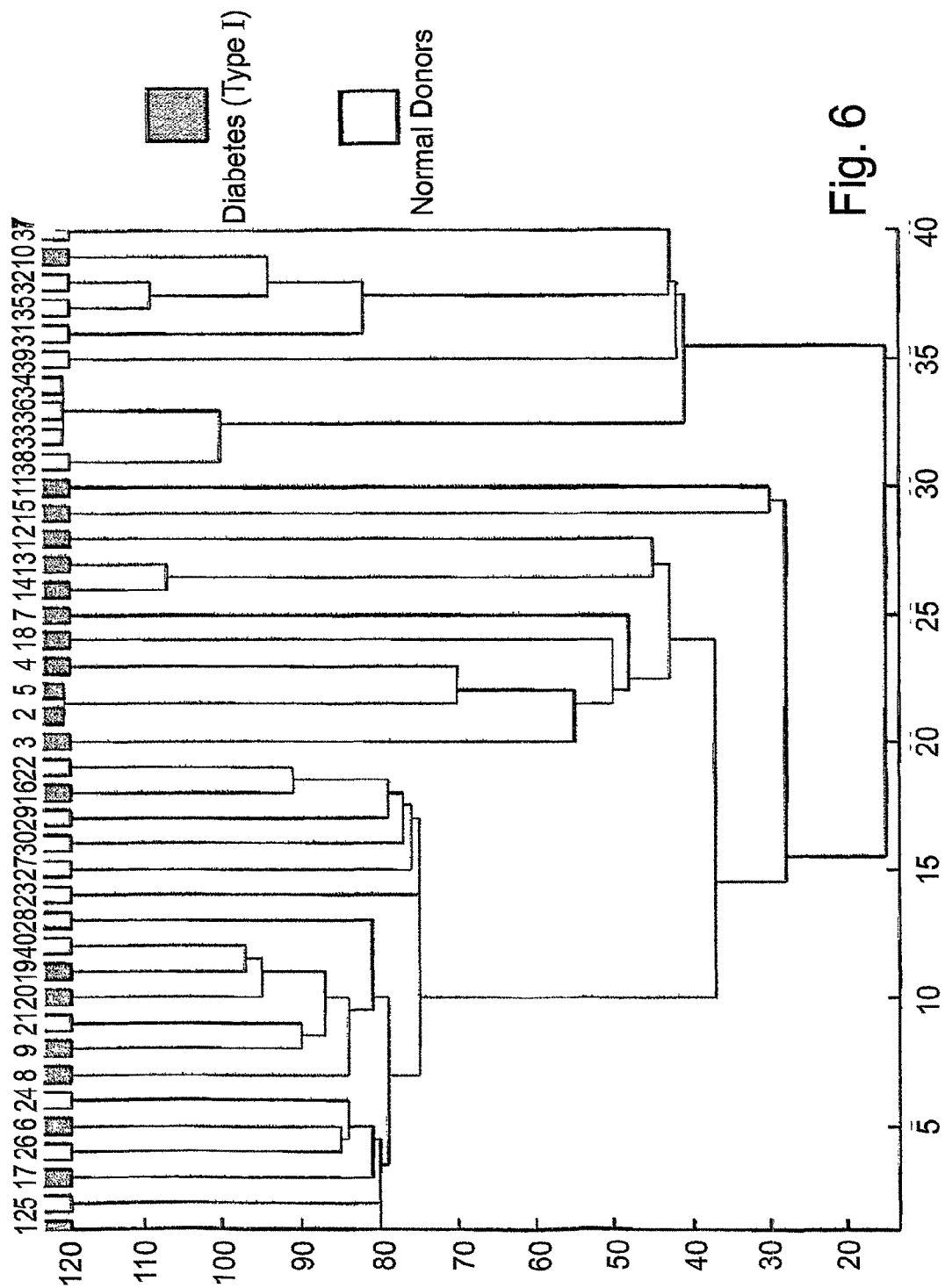
FIG. 6 is a dendrogram created by clustering the subjects over antigen cluster 47. Leaf colors—as in FIG. 2.
Figure 7:
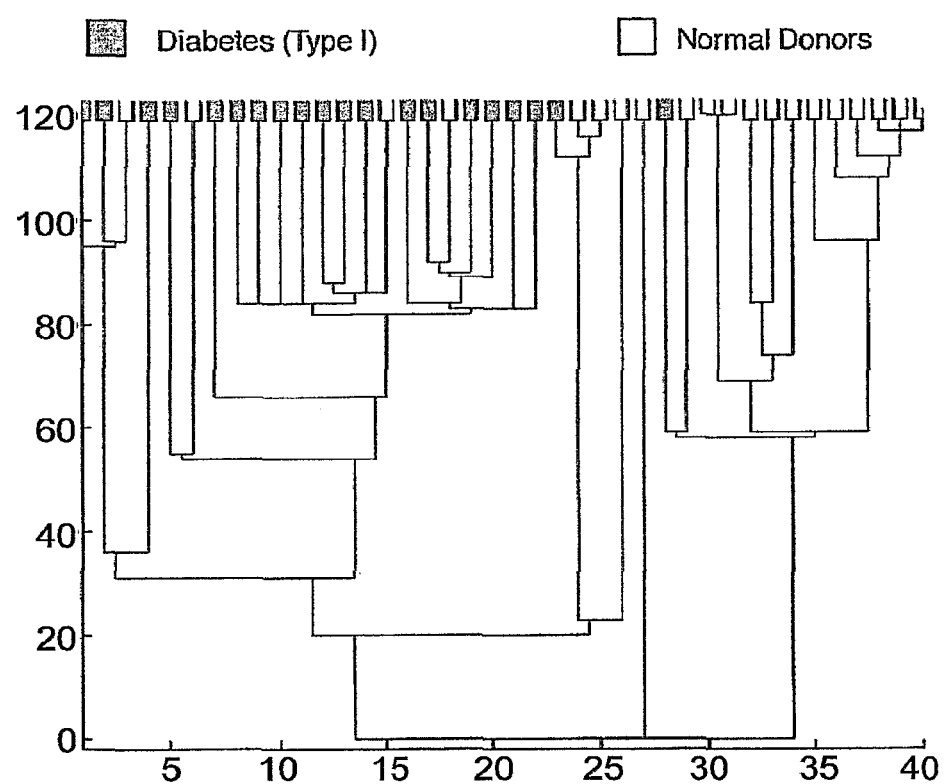
FIG. 7 is a dendrogram created by clustering the subjects over antigen cluster 47. Leaf colors—as in FIG. 2.

Four more antigen clusters were identified as suitable to serve as the feature set for this task: clusters 26, 5, 47 and 14 (see table 3). The last three contain only two antigens each. FIGS. 5, 6 and 7 present the resulting dendrograms for these feature sets. The purity and efficiency of any of the resulting classifications are given in Table 5. None of the above clusters resulted in a high quality classification. It was desired to test whether the classification can be improved by combining the results from all the feature sets. A simple procedure was therefore applied. The clustering results of each of the 5 feature sets were used to diagnose the subjects. For each subject the number of times it was diagnosed as diabetic was counted. Then a 'combined' diagnostics was made, defining all subjects that were diagnosed with diabetes 3 or more times as indeed having diabetes. This simple classification had purity P=19/21=0.90 and efficiency E=19/20=0.95. The method described herein for combining the results and obtaining the diagnosis is relatively naive, and can be much improved using, for example, a multilayer classifier, or any other hierarchical classification method.

This demonstrates the advantage of the Coupled Two Way Clustering which identifies the features that can be found in the data, and separates them into classes (antigen clusters) in order to avoid redundancy. Then one can find which classifications of the data have some correspondence to the desired diagnosis, and combine them in order to obtain most efficient diagnoses.

Example 12

Diabetics Type 1 and 2 Versus Healthy and Year after Treatment

Figure 4:
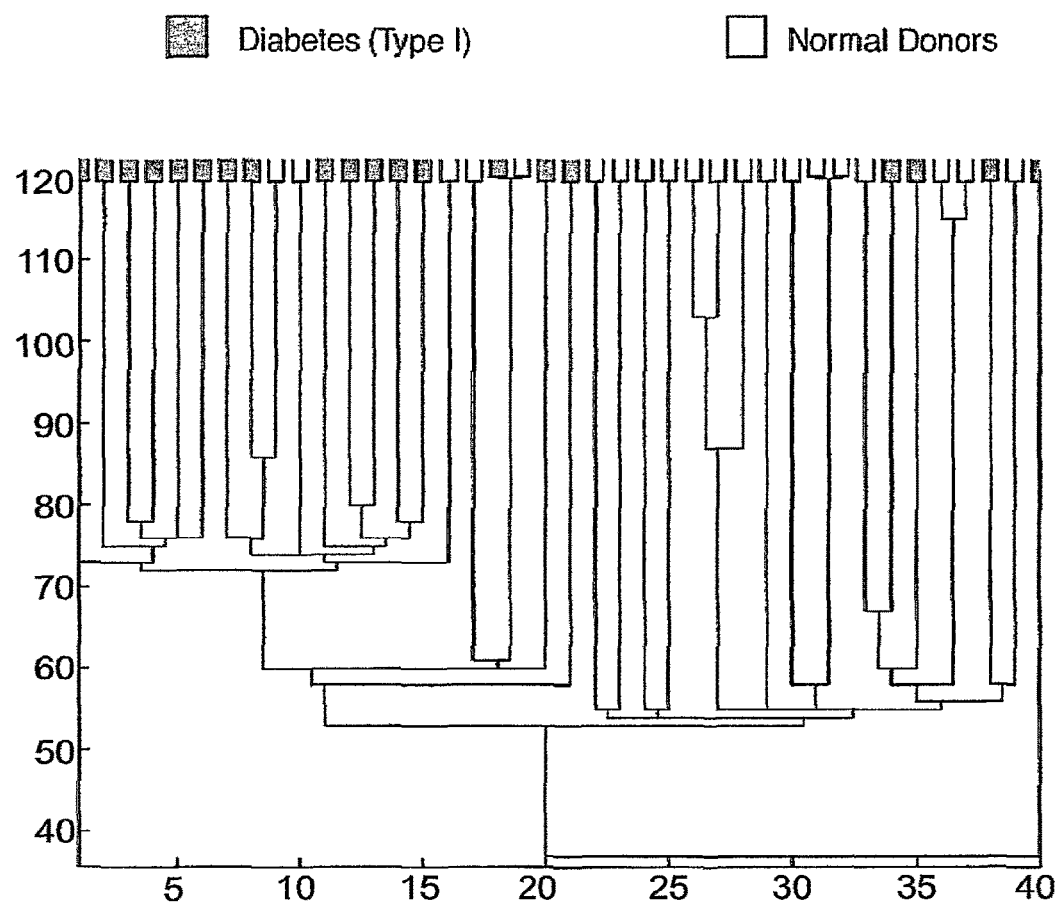
FIG. 4 is a subjects' dendrogram obtained by clustering the subjects, using the antigens of cluster 26. Leaf colors were assigned as in FIG. 2. Antigen cluster 5 contains 2 antigen tests: GM Insulin and GM Aldolase.
Figure 8:
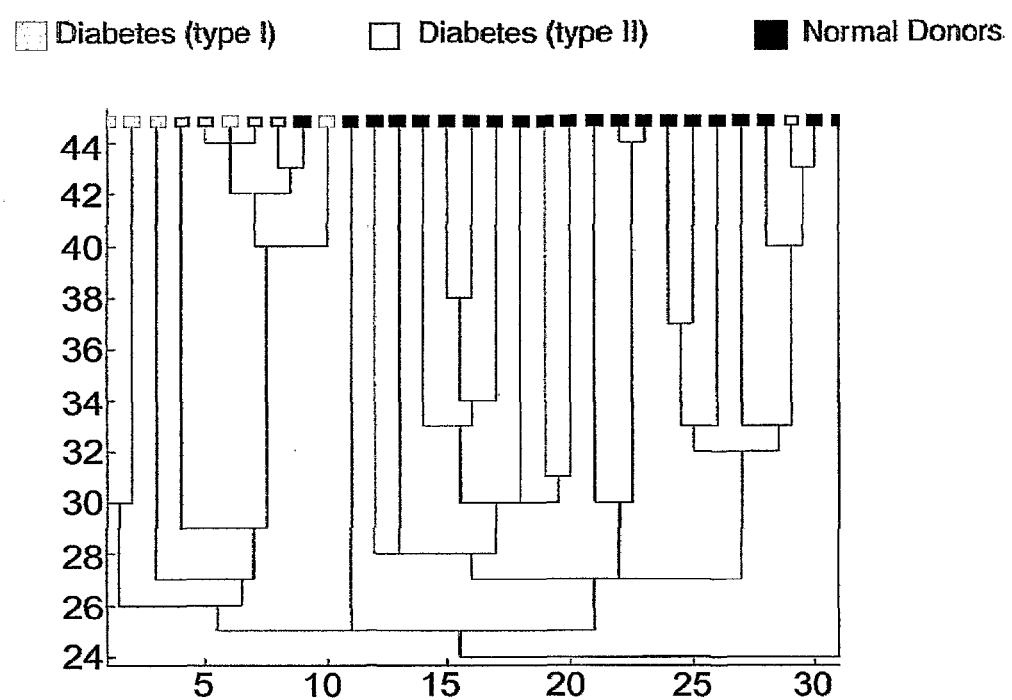
FIG. 8 is a dendrogram created by clustering the subjects over antigen cluster 19, without including the 5 samples corresponding to YL.

Using the same methodology described above, 5 samples taken from patients affected by type I diabetes were studied and compared with 5 samples taken from the same patients after they underwent a year long (YL) treatment with insulin, 5 samples from patients affected by type 2 diabetes (D2) and with 20 samples taken from healthy donors. In this case, IgG and IgM serum reactivities were followed together, without analyzing serum IgM separately. FIG. 8 presents the dendrogram obtained using the antigens of cluster 19 (see FIG. 4) as the feature set, when the samples from the YL group were not included in the analysis. It can be seen that the samples corresponding to the D1 and D2 groups cluster together, separated from the group of healthy samples. Therefore, the antigens of group 19 seem to be extremely useful for diagnostic purposes because they identify D1 and D2 subjects. When the samples of the YL group were added in the study, they were grouped together with those of the healthy donors. Hence, even though initially these subjects were D1, after a year under treatment their reactivity profile (on the group 19 of antigens) has become close to that of healthy subjects.

Example 13

Separation of Diabetics Type 1 from Type 2

Figure 9:
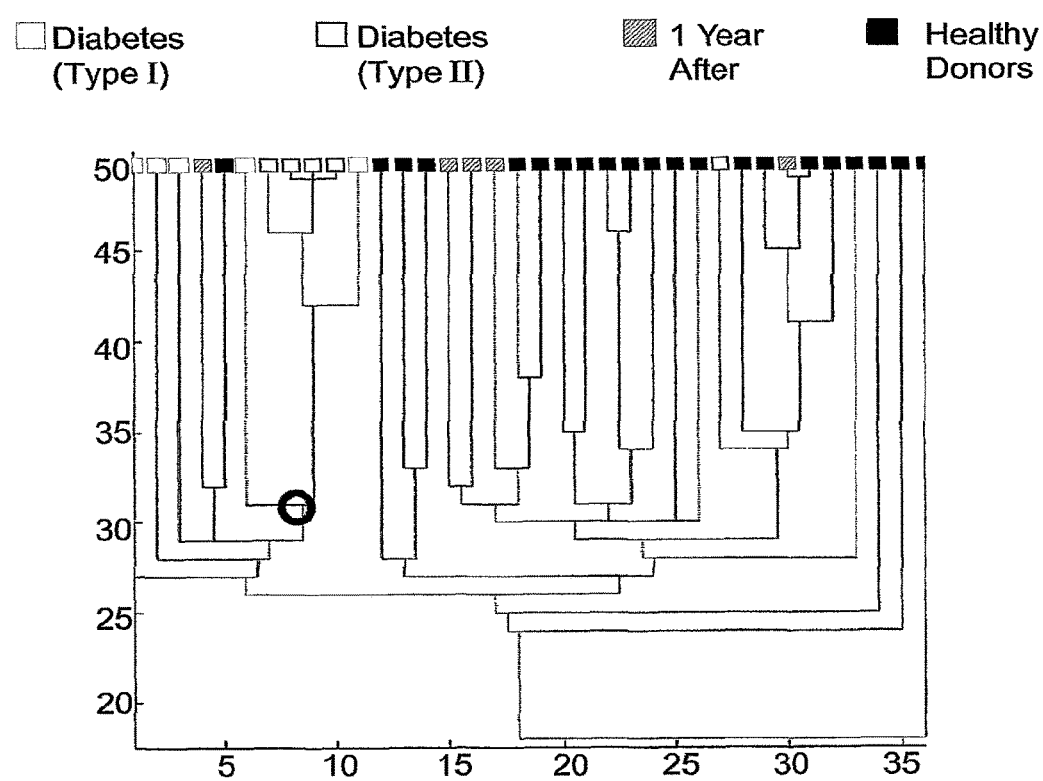
FIG. 9 is a dendrogram created by clustering the subjects over antigen cluster 19, including the 5 samples corresponding to YL. The cluster that contains the D1 and D2 groups is labelled.

As can be seen in FIG. 9, the cluster of the diabetic subjects contains a very clear and stable subcluster, whose members are 4 out of the 5 D2 subjects (yellow) and a single D1 subject. This indicates that the algorithm described herein is capable of separating the D2 from the D1 subjects. See also Table 5, below.

Example 14

Bechet's Disease and Healthy Subjects

A similar experiment was performed with 82 antigens and 49 subjects, among them 28 have Bechet disease (labeled BD) and 21 are healthy (labeled NH). In this case, IgG and IgM serum reactivities were followed together, without analyzing serum IgM separately. FIG. 10 depicts the results obtained when antigen cluster 13 (see Table 3) was used as the feature set. A stable cluster of 23 subjects was identified, of whom 9 are diseased and 14 healthy. A classifier which isolates this cluster and diagnoses all sera outside it as diseased will have purity of P=19/26=0.73 and efficiency of E=19/28=0.68.

Figure 11:
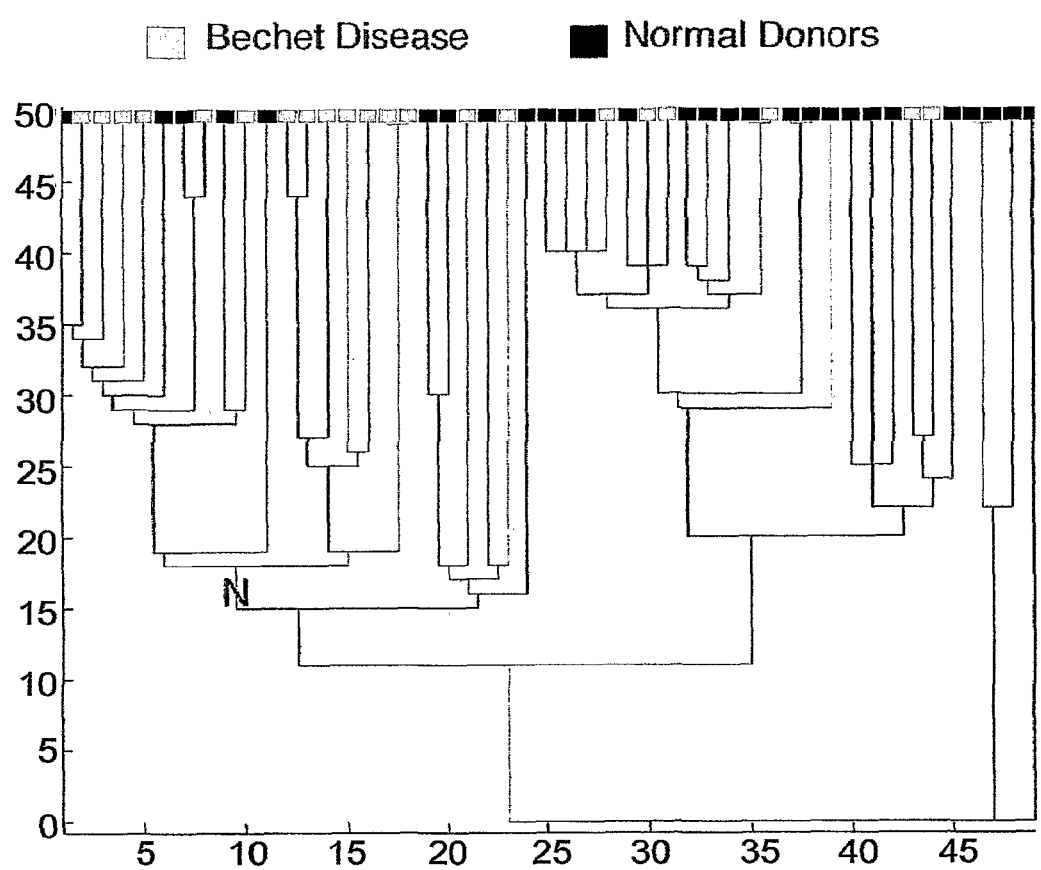
FIG. 11 is a dendogram created by clustering the Bechet Disease samples and the healthy serum samples using antigen cluster 9.

Another antigen cluster that has been identified as suitable to serve as the feature set for this task is No. 9 (see Table 4), which contains only two antigens. FIG. 11 presents the resulting dendrogram; the well defined cluster denoted by NH contains predominantly healthy subjects. Classifying all those that do not belong to it as diseased yields purity of P=23/31=0.74 and efficiency of E=23/28=0.82. Combining the results of both sets of antigens, the cluster analysis identified the BD patients with a sensitivity of 96% and a specificity of 71%.

Example 15

TABLE 5

Summary of results

| Subjects | Compared to | Antigen set | Sensitivity/ Efficiency (E) | Specificity/ Purity (P) | FIG. |
|---|---|---|---|---|---|
| D1 | NH | 66 | 1.00 | 0.69 | 3 |
| | | 26 | 0.65 | 0.81 | 4 |
| | | 5 | 0.75 | 0.83 | 5 |
| | | 47 | 0.55 | 1.00 | 6 |
| | | 14 | 0.95 | 0.70 | 7 |
| | | Combination | 0.95 | 0.90 | |
| D1|D2 | NH | 19 | 0.90 | 0.90 | 8 |
| D1|D2 | NH|YL | 19 | 0.90 | 0.81 | 9 |
| D2 | D1 | 19 | 0.80 | 0.80 | 9 |
| BD | NH | 13 | 0.68 | 0.73 | 10 |
| | | 9 | 0.82 | 0.74 | 11 |
| | | Combination | 0.96 | 0.71 | |

Thus, the method described herein, by simultaneously evaluating several representative antibody autoreactivities, allows the efficient separation of different groups of patients undergoing several autoimmune pathologies (see Table 5 for summary of the results). It was shown that the immune profile of diabetes over 5 different groups of antigens differs from the immune profile of healthy subjects. The difference is reflected in the clustering results, which yield classifications with a relatively high purity and efficiency (see FIGS. 5-7). Most of the misclassified subjects in each classification were classified correctly by most of the other classifications. Thus, by combining the results of all the classifications, a very clear diagnosis was achieved. Furthermore, it is demonstrated that this analysis allows to identify samples obtained from patients affected by non-autoimmune pathologies, as is the case for type II diabetes (Table 5 and FIGS. 8 and 9). In addition, the system described herein can identify dynamic changes associated with the progression of the disease, as demonstrated for type I diabetes patients studied at the moment of diagnosis or 1 year later (Table 5 and FIG. 9).

Finally, it was shown that this analysis can be extended to other diseases where the mechanisms involved, as well as the self-antigens targeted, are not well characterized, as is the case of BD. When BD samples were analysed, it was possible to distinguish BD patients from NHS, using two different set of antigens (FIGS. 10 and 11). Therefore, the combination of the diagnoses based on the reactivities of these two sets of antigens might be used as a tool for the diagnosis of BD, with acceptable levels sensitivity and specificity (0.96 and 0.71 respectively).

Based on the results presented herein, a classifier could be constructed, able to identify an undetermined sample as corresponding to a healthy or diseased subject. This is extremely important for the management of, for example, Bechet's Disease, where no defined antigens have been isolated yet for diagnostic purposes.

Example 16

Construction of Protein (e.g., Antigen) Chips

The results presented above using the ELISA system can easily be made applicable by the implementation of chip based technologies, allowing the analysis of several parameters in a single assay (22, 23). Developments in the field of micro-technology have allowed the construction of protein micro-arrays designed for use in the post genomics era of so-called proteinomics (22-25). However, until now, this technology has not been applied to the analysis of multiple antigen-antibody interactions, which might be used, as it is now shown, for marking the state of the immune system in various conditions of importance.

An antigen chip in accordance with the teachings of the present invention is fabricated as follows: Optically flat, teflon-coated 96-well glass microscope plates (Erie Scientific, Portsmouth, N.H., USA) is activated for protein binding, by treatment with aminopropyltrimethoxysilane (APTS) (Aldrich Chemical, Milwaukee, Wis., USA) and Bis-sulfo-succinimidyl suberate (BS3) (Molecular BioSciences, Boulder, Colo., USA) as described (24). These N-hydroxysuccinimide (NHS) activated plates are then coated with the antigens of interest, in quadruplicates, with the help of a microarray printer including, for example, a 36-capillary array print head mounted to a high resolution X-Y-Z positioning robot (7). This device is able to precisely and simultaneously deliver up to 36 different solutions (200 pl per spot) to the flat surface of the pre-activated glass, generating spots of approximately 275 □m in diameter with a center to center spacing of 300 □m.

The development of the slides can be done according to the methods described by Conway de Macario et al. (26) for the Slide Immuno-Enzymatic Assay (SIA). Briefly, the 96-well microarray plate is washed 3 times with 1× Tris buffered saline (TBS)+0.1% Tween 20 to remove excess unbound antigen. Nonspecific binding sites are blocked with 1% Bovine Serum Albumin (BSA) dissolved in Phosphate buffered saline (PBS). After blocking, the sera to be tested is added, diluted in 1% BSA, and is incubated at room temperature for one hour. Unbound antibodies are removed by washing the microplate 3 times with 1×TBS+0.1% Tween 20. Secondary detection of bound antibody is carried out by incubation of each well with an appropriate dilution of Cy3 or Cy5 (Jackson ImmunoResearch, MA, USA) conjugate in TBS+0.1% Tween 20 for 20 minutes. Excess conjugate is removed by washing 3 times with 1×TBS+0.1% Tween 20. The bound antibody is measured using a GenePix 4000A laser scanner that uses confocal optics (Axon Instruments, Foster City, Calif., USA) and allows the acquisition of 10 micron high-resolution scans (25). GenePix 2.0 (Axon Instruments, Foster City, Calif., USA), a software specifically designed to be used with the scanner, is used in order to control the equipment and handle the data. Finally, for each microarray a matrix is obtained, which matrix is later on analyzed with the clustering methods described hereinabove. Obviously, chips using larger numbers of antigen wells can be used for the purposes of the present invention and the entire procedure automated by computer control.

These techniques can be slightly modified to allow analysis of systems other than the immune system. The spot of the purified antigens or protein products of expression libraries generated, for example, from human or other sources of cDNA (23) are spotted on a PVDF membrane by a robotic system, and later on they are developed using the same methodology described above for glass-mounted microarrays and are thereafter analyzed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Sakane, T., M. Takeno, N. Suzuki, and G. Inaba. 1999. Bechet's disease. *N Engl J Med* 341:1284.
2. Tisch, R., and H. McDevitt. 1996. Insulin-dependent diabetes mellitus. *Cell* 85:291.
3. Magsaam, J., A. E. Gharavi, A. P. Parnassa, H. Weissbach, N. Brot, and K. B. Elkon. 1989. Quantification of lupus anti-ribosome P antibodies using a recombinant P2 fusion protein and determination of the predicted amino acid sequence of the autoantigen in patients' mononuclear cells. *Clin Exp Immunol* 76:165.
4. Reichlin, M., T. F. Broyles, O. Hubscher, J. James, T. A. Lehman, R. Palermo, H. A. Stafford, E. Taylor-Albert, and M. Wolfson-Reichlin. 1999. Prevalence of autoantibodies to ribosomal P proteins in juvenile-onset systemic lupus erythematosus compared with the adult disease. *Arthritis Rheum* 42:69.
5. Stafford, H. A., C. J. Anderson, and M. Reichlin. 1995. Unmasking of anti-ribosomal P autoantibodies in healthy individuals. *J Immunol* 155:2754.
6. Pers, J., C. Jamin, F. Predine-Hug, P. Lydyard, and P. Youinou. 1999. The role of CD5-expressing B cells in health and disease. *Int J Mol Med* 3:239.
7. Coutinho, A., M. D. Kazatchkine, and S. Avrameas. 1995. Natural autoantibodies. *Curr Opin Immunol* 7:812.
8. Kyriatsoulis, A., M. Manns, G. Gerken, A. W. Lohse, W. Ballhausen, K. Reske, and K. H. Meyer zum Buschenfelde. 1987. Distinction between natural and pathological autoantibodies by immunoblotting and densitometric subtraction: liver-kidney microsomal antibody (LKM) positive sera identify multiple antigens in human liver tissue. *Clin Exp Immunol* 70:53.
9. Baslund, B., and J. Wieslander. 1994. A rapid and semi-quantitative method for the detection of autoantibodies by multiple spot immunoassay [see comments]. *J Immunol Methods* 169:183.
10. Haury, M., A. Grandien, A. Sundblad, A. Coutinho, and A. Nobrega. 1994. Global analysis of antibody repertoires. 1. An immunoblot method for the quantitative screening of a large number of reactivities. *Scand J Immunol* 39:79.
11. Nobrega, A., M. Haury, A. Grandien, E. Malanchere, A. Sundblad, and A. Coutinho. 1993. Global analysis of antibody repertoires. H. Evidence for specificity, self-selection and the immunological "homunculus" of antibodies in normal serum. *Eur J Immunol* 23:2851.
12. Bouanani, M., G. Dietrich, V. Hurez, S. V. Kaveri, M. Del Rio, B. Pau, and M. D. Kazatchkine. 1993. Age-related changes in specificity of human natural autoantibodies to thyroglobulin. *J Autoimmun* 6:639.
13. Hurez, V., S. V. Kaveri, and M. D. Kazatchkine. 1993. Expression and control of the natural autoreactive IgG repertoire in normal human serum. *Eur J Immunol* 23:783.
14. Mahana, W., B. Guilbert, and S. Avrameas. 1988. Regulation of the humoral immune response by polyspecific natural autoantibodies. *Ann Inst Pasteur Immunol* 139:349.
15. Hartigan, J. 1975. *Clustering Algorithms*. Wiley, New York.
16. Dubes, J. a. R. C. 1988. *Algorithms for Clustering Data*. Prentice-Hall, Englewood Cliffs.
17. Kohonen. 1997. *Self-Organizing Maps*. Springer, Berlin.
18. Blatt, M., S. Wiseman, and E. and Domany. 1996. Super-paramagnetic clustering of data. *Physical Review Letters* 76:3251.
19. U.S. Pat. No. 6,021,383.
20. Getz, G., E. Levine, and a. D. E. Coupled two way clustering of gene microarray data. *Submitted*.
21. Israel Patent Application No. 2000-044.
22. Duggan, D. J., M. Bittner, Y. Chen, P. Meltzer, and J. M. Trent. 1999. Expression profiling using cDNA microarrays. *Nat Genet* 21:10.
23. Lucking, A., H. Horn, H. Eickhoff, K. Bussow, H. Lehrach, and G. Walter. 1999. Protein microarrays for gene expression and antibody screening. *Anal Biochem* 270:103.
24. Mendoza, L. G., P. McQuary, A. Mongan, R. Gangadharan, S. Brignac, and M. Eggers. 1999. High-throughput microarray-based enzyme-linked immunosorbent assay (ELISA). *Biotechniques* 27:778.
25. De Risi, J. L., V. R. Iyer, and P. O. Brown. 1997. Exploring the metabolic and genetic control of gene expression on a genomic scale. *Science* 278:680.
26. Conway de Macario, E., R. J. Jovell, and A. J. Macario. 1987. Slide mmunoenzymatic assay (SIA): improving sensitivity to measure antibodies when samples are very small and dilute, and antigen is scarce. *J Immunoassay* 8:283.

What is claimed is:

1. A method of clustering a subset of antigens of a plurality of antigens, said subset of antigens being reactive with a plurality of antibodies being derived from a plurality of patients having a disease, whereby the disease is associated with autoantibodies, the method comprising the steps of:
   (a) providing a plurality of test antigens, said test antigens being self-antigens or antigens from a library;
   (b) assaying binding of said plurality of antibodies being derived from said plurality of patients with said plurality of antigens;
   (c) assaying binding of a plurality of antibodies being derived from a plurality of individuals free of said disease with said plurality of antigens; and
   (d) bioinformatically clustering a subset of antigens exhibiting an immune reactivity with said plurality of antibodies being derived from said plurality of patients having said disease, wherein said immune reactivity of (b) is classified as different from that exhibited with said plurality of antibodies being derived from said individuals free of said disease of (c).

2. The method of claim 1, wherein said step of clustering is effected so as to include in said subset of antigens those antigens for which said patients and individuals best decompose into clusters according to a known clinical diagnosis of said patients and individuals.

3. The method of claim 1, wherein said step of clustering is effected by a supervised classifier.

4. The method of claim 3, wherein said supervised classifier is a neural network algorithm.

5. The method of claim 1, wherein said step of clustering is effected by an unsupervised classifier.

6. The method of claim 5, wherein said unsupervised classifier is a coupled two way clustering algorithm or super-paramagnetic clustering.

7. The method of claim 1, wherein said step of clustering is effected so as to result in optimal sensitivity.

8. The method of claim 1, wherein said step of clustering is effected so as to result in optimal specificity.

9. The method of claim 1, wherein said step of clustering is effected so as to result in optimal specificity and optimal sensitivity.

10. The method of claim 1, wherein said step of clustering is effected by:
   (i) clustering said antibodies and said antigens and identifying all stable antibody and antigen clusters;
   (ii) scanning said antigen clusters, while using reactivity levels of antigens of each antigen cluster as a feature set representing first object sets containing either all of said antibodies or any of said stable antibody clusters;
   (iii) scanning said antibody clusters, while using reactivity levels of antibody of each antibody cluster as a feature set representing second object sets containing either all of said antigens or any of said stable antigen clusters;
   (iv) tracking all antibody and antigen stable clusters thus generated;
   (v) repeating steps (i)-(iv) until no new antibody and antigen stable clusters being generated, thereby obtaining final stable antigens and antibody clusters and pointers identifying how all of said stable antibody and antigen clusters have been generated.

11. The method of claim 1, wherein said disease is selected from the group consisting of an autoimmune disease, a cancer, an immune deficiency disease, a degenerative disease, a metabolic disease, an infectious disease, a genetic disease, a mental disorder, an organ transplantation, an injury or an intoxication, or any condition involving cytokines or inflammation.

12. A method of diagnosing a disease of a subject, the method comprising the steps of:

(a) providing a plurality of test antigens;
(b) clustering a subset of antigens of said plurality of test antigens, said test antigens being self-antigens or auto-antigens from a library, said subset of antigens being reactive with a plurality of antibodies being derived from a plurality of patients suffering from said disease by:
  (i) assaying binding of said plurality of antibodies being derived from said plurality of patients with said plurality of test antigens;
  (ii) assaying binding of a plurality of antibodies being derived from a plurality of individuals free of said disease with said plurality of test antigens; and
  (iii) bioinformatically clustering said subset of antigens exhibiting an immune reactivity with said plurality of antibodies being derived from said plurality of patients having said disease of (i), wherein said immune reactivity is classified as different from that exhibited with said plurality of antibodies being derived from said individuals free of said disease of (ii); and
(c) associating or deassociating the antibodies of said subject with a cluster resulting from step (b)(iii).

13. The method of claim 12, wherein said step of clustering is effected so as to include in said subset of antigens those antigens for which said patients and individuals best decompose into clusters according to a known clinical diagnosis of said patients and individuals.

14. The method of claim 12, wherein said step of clustering is effected by a supervised classifier.

15. The method of claim 14, wherein said supervised classifier is a neural network algorithm.

16. The method of claim 12, wherein said step of clustering is effected by a unsupervised classifier.

17. The method of claim 16, wherein said unsupervised classifier is a coupled two way clustering algorithm or super-paramagnetic clustering.

18. The method of claim 12, wherein said step of clustering is effected so as to result in optimal sensitivity.

19. The method of claim 12, wherein said step of clustering is effected so as to result in optimal specificity.

20. The method of claim 12, wherein said step of clustering is effected so as to result in optimal specificity and optimal sensitivity.

* * * * *